(12) United States Patent
Li et al.

(10) Patent No.: US 10,300,484 B2
(45) Date of Patent: May 28, 2019

(54) HANDHELD FLUID HANDLING SYSTEMS AND METHODS

(71) Applicants: Zhenyu Li, McLean, VA (US); Baichen Li, Fairfax, VA (US)

(72) Inventors: Zhenyu Li, McLean, VA (US); Baichen Li, Fairfax, VA (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 190 days.

(21) Appl. No.: 15/128,207

(22) PCT Filed: Mar. 26, 2015

(86) PCT No.: PCT/US2015/022761
§ 371 (c)(1),
(2) Date: Sep. 22, 2016

(87) PCT Pub. No.: WO2015/148808
PCT Pub. Date: Oct. 1, 2015

(65) Prior Publication Data
US 2017/0095810 A1   Apr. 6, 2017

Related U.S. Application Data

(60) Provisional application No. 61/970,699, filed on Mar. 26, 2014.

(51) Int. Cl.
*B01L 3/00* (2006.01)
*F04B 43/04* (2006.01)
(Continued)

(52) U.S. Cl.
CPC ..... *B01L 3/50273* (2013.01); *B01L 3/502715* (2013.01); *B01L 3/502738* (2013.01);
(Continued)

(58) Field of Classification Search
CPC .............. B01L 3/50273; B01L 2300/14; F17C 2205/0138; F17C 2205/0142
(Continued)

(56) References Cited

U.S. PATENT DOCUMENTS 3,044,481 A * 7/1962 Regan ..................... E21B 33/06
137/114
3,797,516 A * 3/1974 Forster ..................... F02C 9/24
137/340

(Continued)

FOREIGN PATENT DOCUMENTS

WO   WO 2015/148808 A1   10/2015

OTHER PUBLICATIONS

Grover, William H., et al. "Monolithic membrane valves and diaphragm pumps for practical large-scale integration into glass microfluidic devices." Sensors and Actuators B: Chemical (2003); 89.3: 315-323.

(Continued)

*Primary Examiner* — Kevin F Murphy
(74) *Attorney, Agent, or Firm* — Cooley LLP

(57) ABSTRACT

A handheld system includes a reference pressure source configured to generate a reference pressure. The handheld system also includes a primary pressure source coupled to the reference pressure source. The primary pressure source is configured to generate a primary pressure in a primary pressure range. The primary pressure is less than the reference pressure, and the primary pressure is induced by the reference pressure source. The handheld system also includes a secondary pressure source coupled to the primary pressure source. The secondary pressure source is configured to generate a secondary pressure in a secondary pressure range. The secondary pressure is less than the primary pressure, and the secondary pressure is induced by the primary pressure source.

22 Claims, 25 Drawing Sheets

(51) Int. Cl.
*G05D 7/06* (2006.01)
*G05D 16/20* (2006.01)
*G01N 35/00* (2006.01)
*G01N 35/10* (2006.01)
*G01N 15/14* (2006.01)

(52) U.S. Cl.
CPC ..... *F04B 43/043* (2013.01); *G01N 35/00871* (2013.01); *G05D 7/0694* (2013.01); *G05D 16/2013* (2013.01); *G05D 16/2026* (2013.01); *B01L 2200/10* (2013.01); *B01L 2200/146* (2013.01); *B01L 2200/16* (2013.01); *B01L 2300/024* (2013.01); *B01L 2300/123* (2013.01); *B01L 2300/14* (2013.01); *B01L 2400/0487* (2013.01); *B01L 2400/0666* (2013.01); *G01N 15/1484* (2013.01); *G01N 2035/00237* (2013.01); *G01N 2035/1034* (2013.01)

(58) Field of Classification Search
USPC ............ 138/30, 31; 137/111, 114, 255–267, 137/505.12, 571, 572
See application file for complete search history.

(56) References Cited

U.S. PATENT DOCUMENTS

| | | | |
|---|---|---|---|
| 4,858,883 A | 8/1989 | Webster et al. | |
| 4,923,008 A * | 5/1990 | Wachowicz | E21B 29/08 137/14 |
| 4,976,162 A | 12/1990 | Kamen | |
| 5,593,130 A | 1/1997 | Hansson et al. | |
| 7,426,935 B2 * | 9/2008 | Schwan | F17C 7/00 137/255 |
| 7,957,927 B2 | 6/2011 | Huitt et al. | |
| 8,104,515 B2 | 1/2012 | Unger et al. | |
| 8,105,265 B2 | 1/2012 | Demers et al. | |
| 8,122,901 B2 * | 2/2012 | Zeng | B01L 3/502738 137/14 |
| 2003/0194328 A1 | 10/2003 | Bryant et al. | |
| 2012/0329142 A1 * | 12/2012 | Battrell | B01F 11/0071 435/287.2 |
| 2013/0240068 A1 * | 9/2013 | Samara-Rubio | F15B 1/24 137/571 |

OTHER PUBLICATIONS

Hosokawa, Kazuo, and Maeda, Ryutaro. "A pneumatically-actuated three-way microvalve fabricated with polydimethylsiloxane using the membrane transfer technique." Journal of Micromechanics and Microengineering (2000); 10.3: 415.

Tan, Wei-Heong, and Takeuchi, Shoji. "A trap-and-release integrated microfluidic system for dynamic microarray applications." Proceedings of the National Academy of Sciences (2007); 104.4: 1146-1151.

Unger, Marc A., et al. "Monolithic microfabricated valves and pumps by multilayer soft lithography." Science (2000); 288.5463: 113-116.

International Search Report and Written Opinion for International Application No. PCT/US2015/022761, dated Aug. 17, 2015, 15 pages.

International Preliminary Report on Patentability for International Application No. PCT/US2015/022761, dated Sep. 27, 2016, 12 pages.

* cited by examiner

1. Sealed with PDMS
2. Small Internal Volume

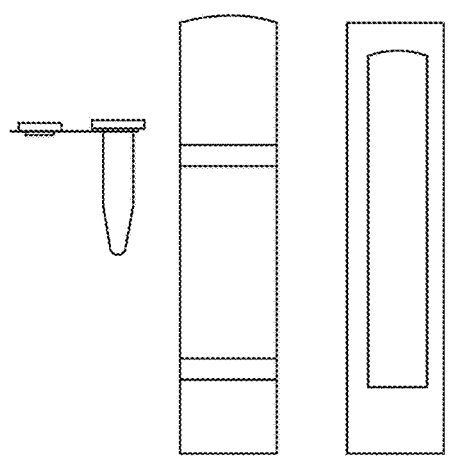
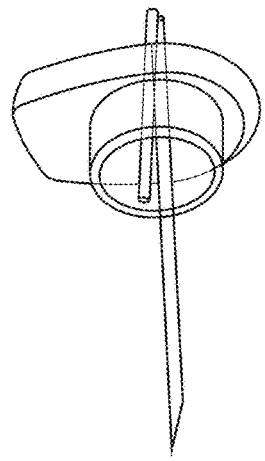
FIG. 19A FIG. 19B
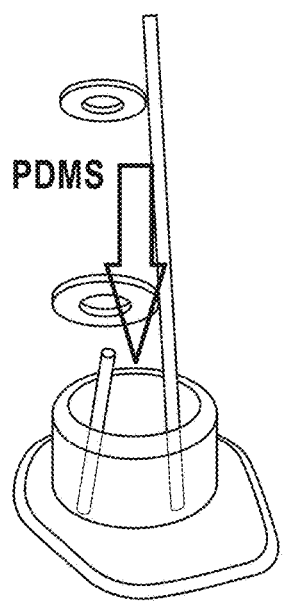
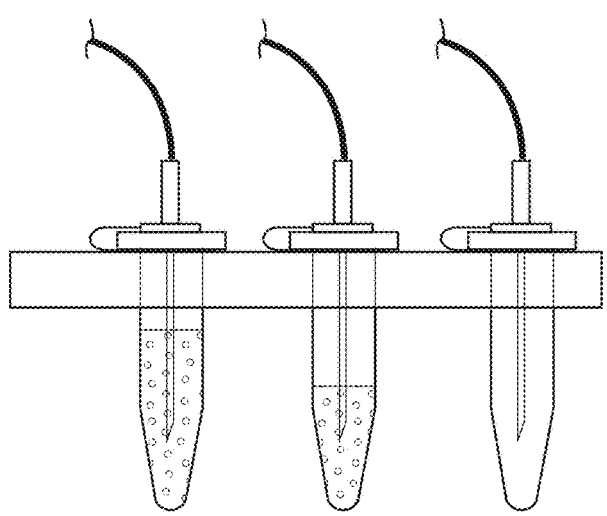
FIG. 19C FIG. 19D

GW Handheld Microfluidics

| ASSAYS | TEST |

Valve Test

| #1 | #2 | #3 | #4 | #5 |
| #6 | #7 | #8 | | 〰️ |

Target Pressure Settings

P1 Range : [5] [7] PSI
P2 Range : [1.9] [2.1] PSI

[Update Settings] [P2+0] [ZERO ALL]

Pressure Monitor

Pressure 1    505    10.10
Pressure 2    96    1.92

[Record]

FIG.20C

HANDHELD FLUID HANDLING SYSTEMS AND METHODS

CROSS-REFERENCE TO RELATED APPLICATIONS

This application is a U.S. National Phase of PCT/US2015/022761, filed Mar. 26, 2015 and claims priority to U.S. provisional application No. 61/970,699 titled "HANDHELD PNEUMATIC FLUIDIC HANDLING SYSTEM", filed Mar. 26, 2014, the entire disclosure of which is incorporated herein by reference in its entirety.

BACKGROUND

One goal of lab-on-a-chip research is to miniaturize and/or scale biological and chemical instruments into chip formats. Such instruments usually require, or rely on, the handling of liquids samples such as blood, urine, on liquid reagents, and/or the like. Therefore, it is desirable for lab-on-a-chip systems to have built-in liquid handling capabilities to achieve self-contained sample processing capabilities. However, due to various challenges, few handheld, self-contained systems capable of complex liquid handling exist in the market today.

SUMMARY

A handheld system includes a reference pressure source configured to generate a reference pressure. The handheld system also includes a primary pressure source coupled to the reference pressure source. The primary pressure source is configured to generate a primary pressure in a primary pressure range. The primary pressure is less than the reference pressure, and the primary pressure is induced by the reference pressure source. The handheld system also includes a secondary pressure source coupled to the primary pressure source. The secondary pressure source is configured to generate a secondary pressure in a secondary pressure range. The secondary pressure is less than the primary pressure, and the secondary pressure is induced by the primary pressure source.

BRIEF DESCRIPTION OF THE DRAWINGS

FIG. 8A illustrates the reservoir with a solenoid valve in a first configuration. FIG. 8B illustrates the reservoir with the solenoid valve in a second configuration, such that the volume of the reservoir is increased, and the pressure in the reservoir is reduced. FIG. 8C illustrates the reservoir with the solenoid valve reverted to the first configuration after the desired reduction in pressure is achieved.

FIG. 14A illustrates the performance test of P1. The target pressure range of P1 was set to 13-14 psi. The plot shows the reading from Barometric Sensor 1 over 300 s. FIG. 14B illustrates the performance test of P2. With P1 set to 13-14 psi, P2 was tested under four different target pressure levels: 1, 2, 3, and 4 psi (four colored curves), with a tolerance of ±0.05 psi. Meanwhile, one on-chip valve was opened to allow a reagent (colored food dye) to be driven into the microfluidic chip. Every test lasted for 10 minutes. The target pressure was set to 0 psi on completion of the test.

FIGS. 16A-16C3 illustrates an example two-layered PDMS microfluidic device for bead-based immunoassays, and demonstration of immunoassay liquid handling. FIG. 16A illustrates the design layout of the microfluidic device for bead-based immunoassays. Inset: magnified view of the hydrodynamic trap assays with one trapped microbead. FIGS. 16B1-16B3 illustrate washing and incubating the immobilized microbeads with different reagents. Two colored dyes and water were used to simulate different reagents in an immunoassay. FIGS. 16C1-16C3 illustrate optical micrographs of an array of microbeads in the traps. Microbeads of 15 μm diameter are loaded before the experiment. Optical micrographs showing the trapped microbeads being washed (or incubated) with different colored liquids.

Vertical dashed lines (marked with numbers in a box) indicate the starting points of the various immunoassay steps of Table 3.

Figure 7A:
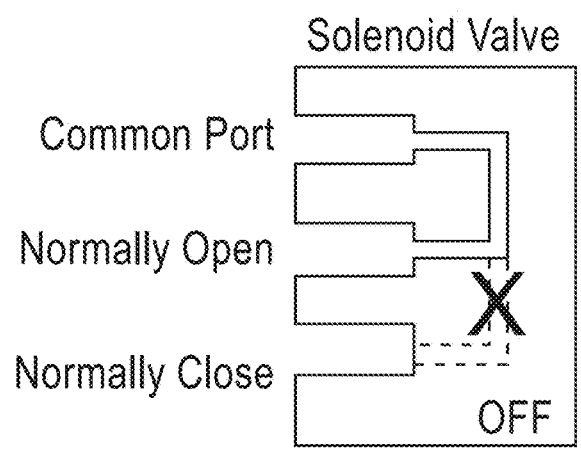
FIGS. 7A-7B are example illustration of a solenoid valve in an "OFF" state (FIG. 7A) and an "ON" state.
Figure 7B:
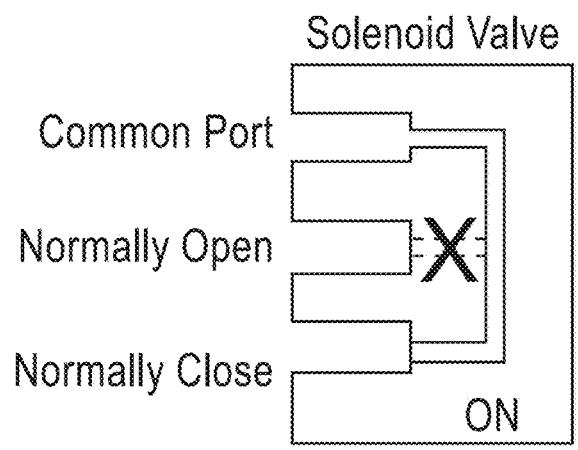
Figure 13:
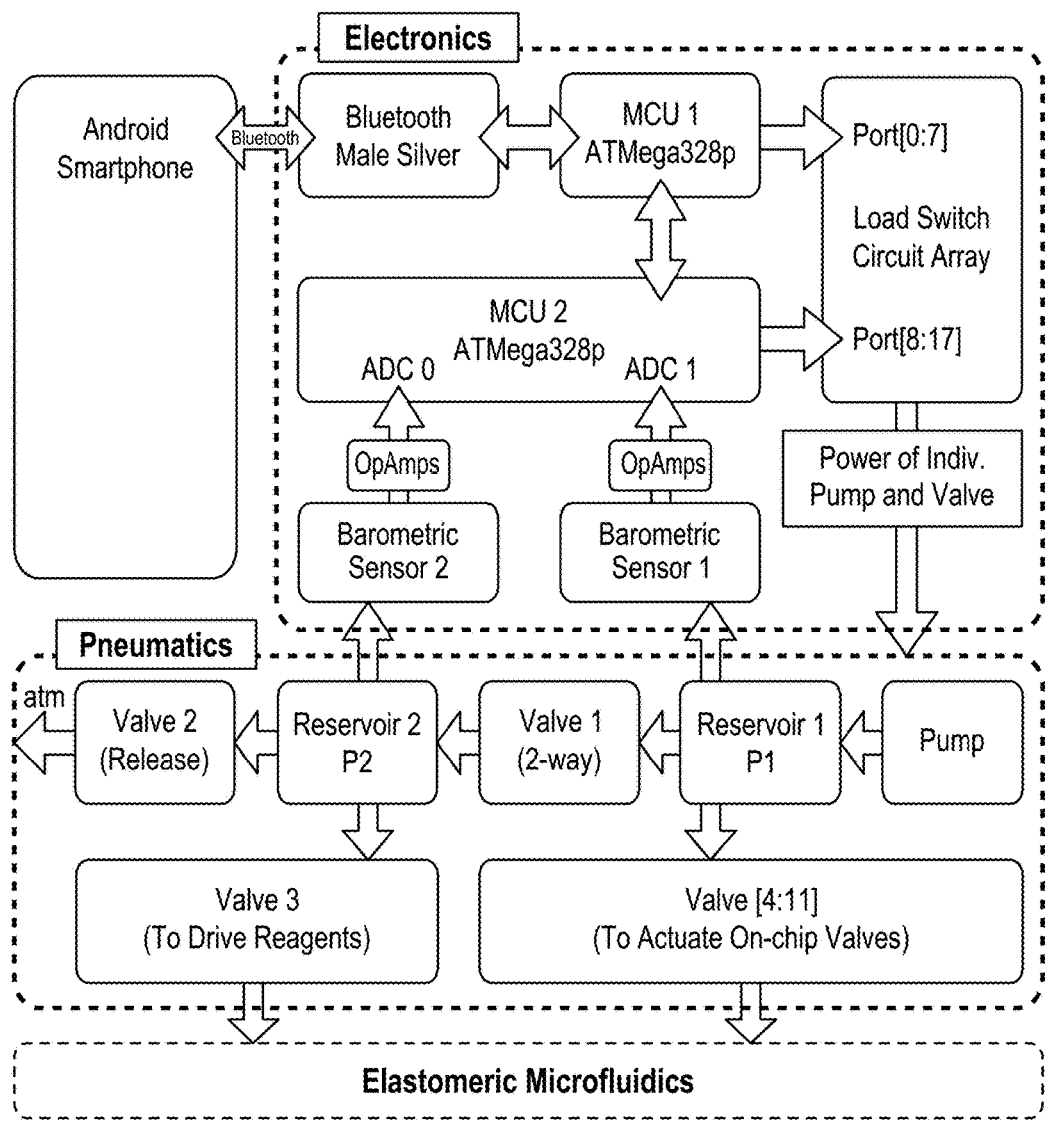
FIG. 13 is a block diagram of an example system. The system consists of an Android smartphone, an electronic PCB with microcontrollers and Bluetooth module, and a pneumatic system capable of generating two different pressure output. Valve 1 is a two-way normally closed solenoid valve and Valves 2 to 11 are three-way solenoid valves.
Figure 18A:
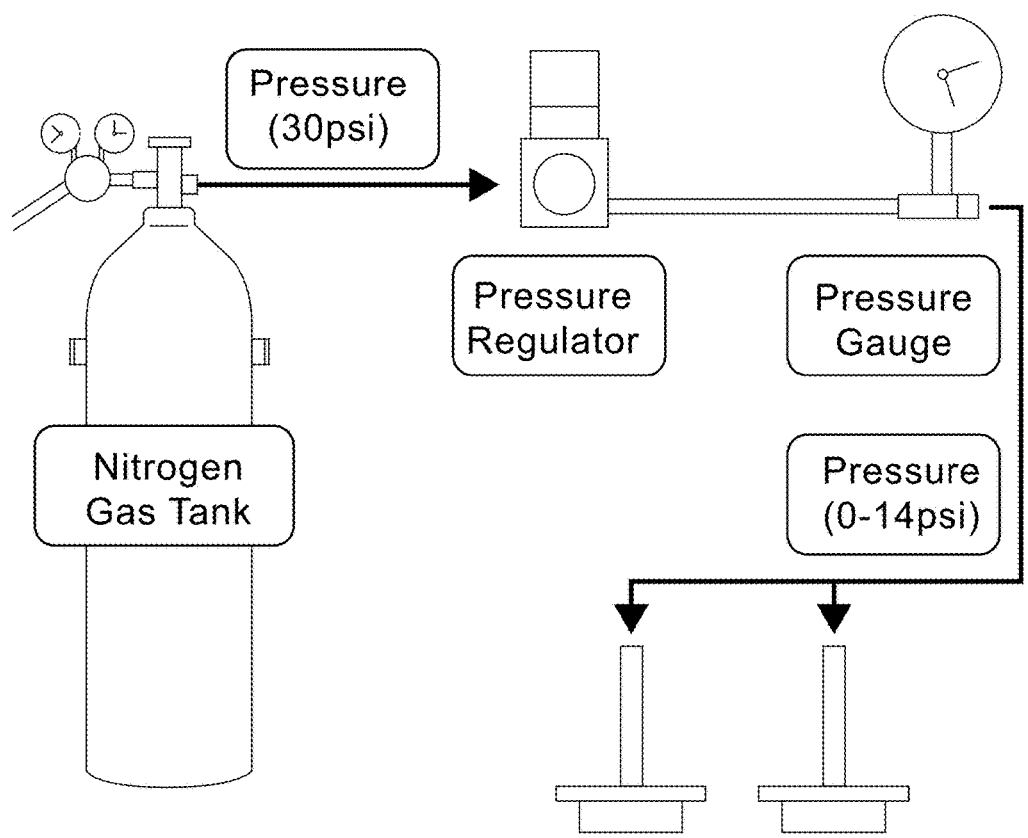
Figure 18B:
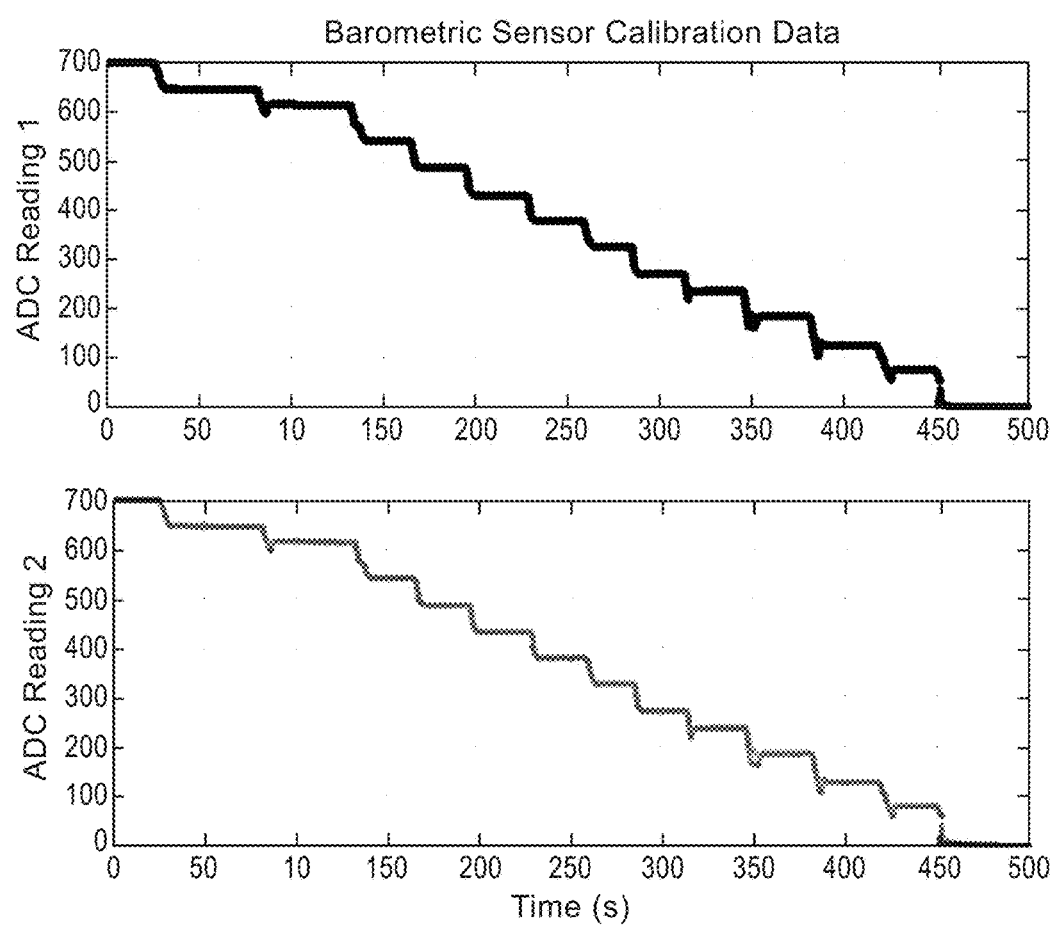
Figure 18D:
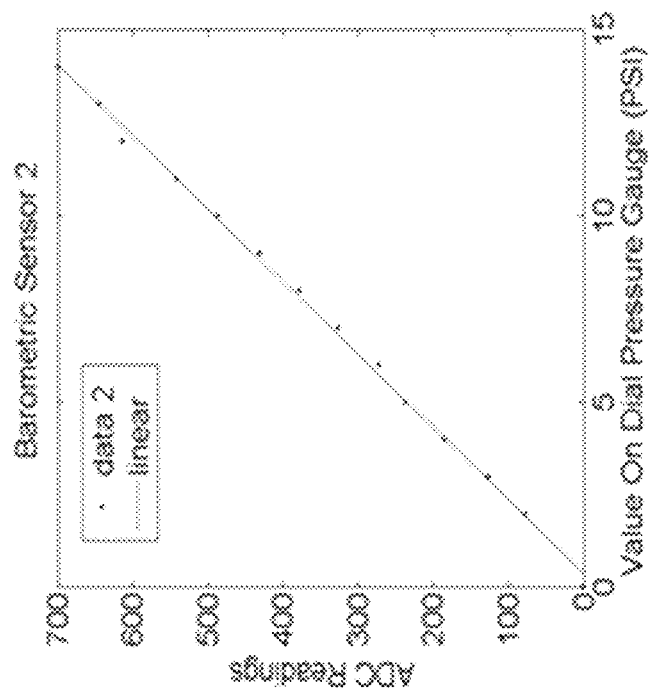
Figure 18C:
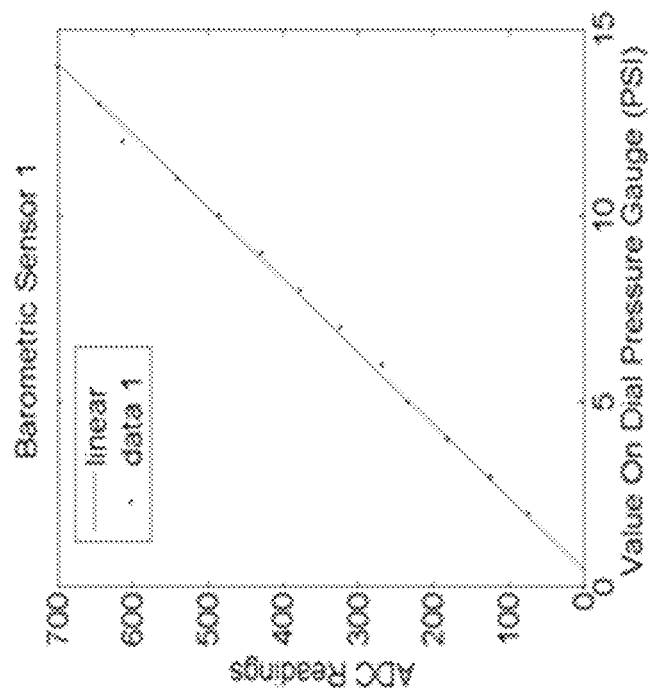

FIGS. 18A-18D illustrate determination of the small volume of the solenoid valve of FIGS. 7A-7B. FIG. 18A illustrates an example barometric sensor calibration setup. FIG. 18B illustrates recorded data of ADC readings for calibration. FIG. 18C illustrates an example calibration curve of barometric Sensor 1 of FIG. 13. FIG. 18D illustrates an example calibration curve of barometric Sensor 2 of FIG. 13.

FIGS. 19A-19D illustrate an example fabrication of reagent containers. FIG. 19A illustrates a microcentrifuge tube with a lid used for holding a reagent. FIG. 19B illustrates the lid of the microcentrifuge tube pierced by needles. FIG. 19C illustrates sealing of the lid with PDMS. FIG. 19D illustrates microcentrifuge tubes filled with reagents and connected with tubing to a fluid handling system.

Figure 20A:
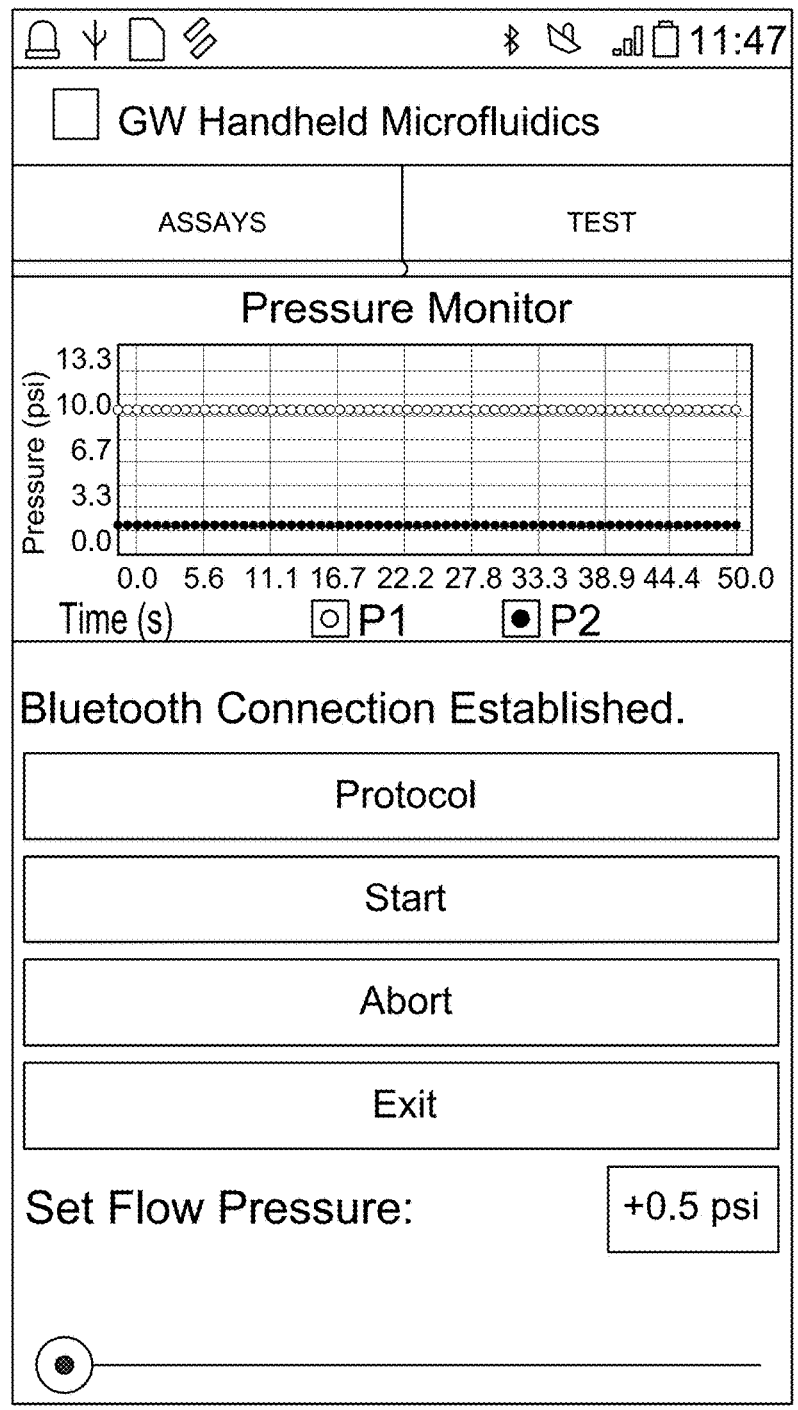
Figure 20B:
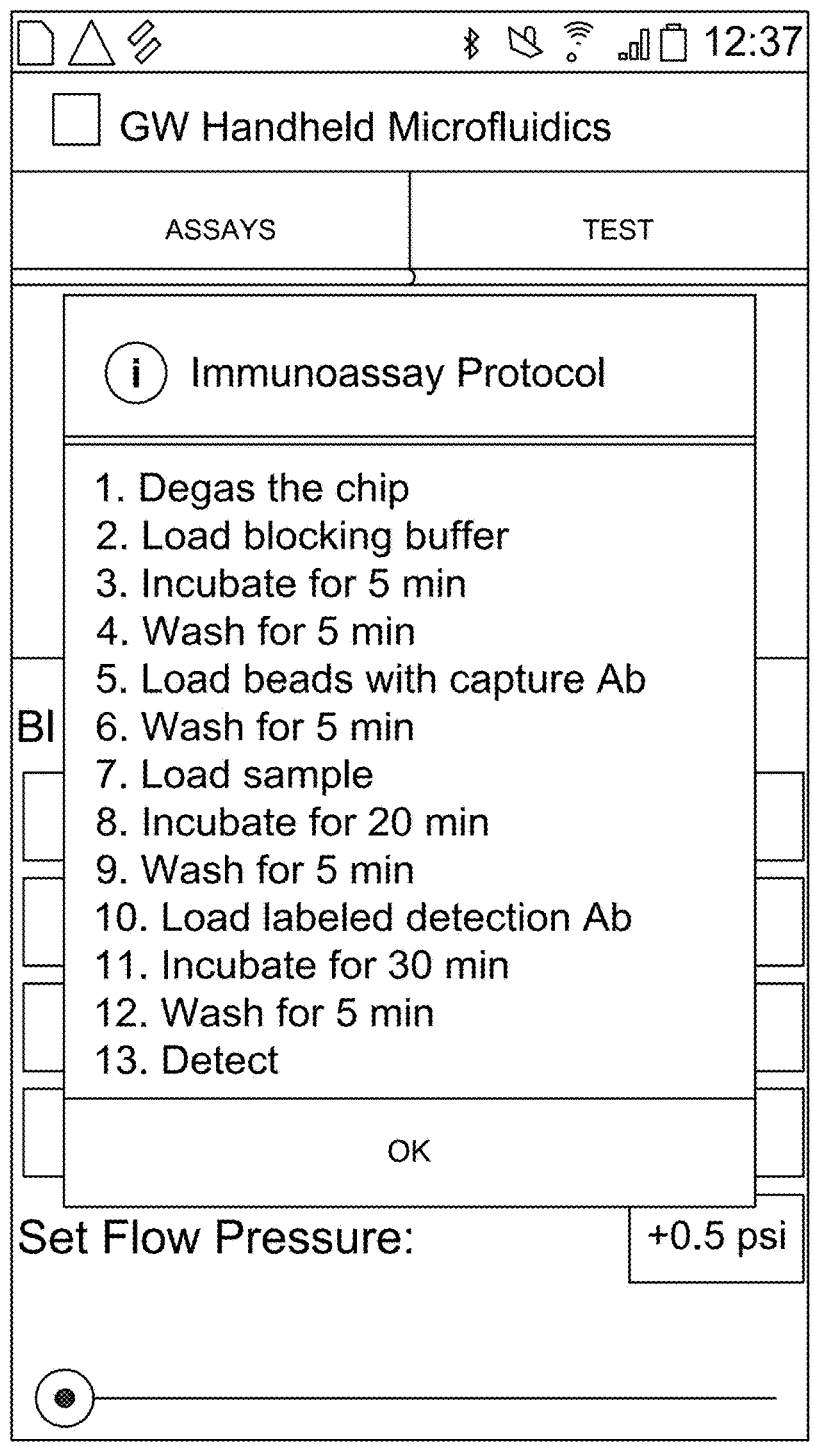

FIGS. 20A-20C illustrate example user interfaces of a software application for operation of a handheld system. FIG. 20A illustrates the collection of real-time pressure data. FIG. 20B illustrates an immunoassay protocol displayed to a user. FIG. 20C illustrates protocol settings, and pressure output.

Figure 21:
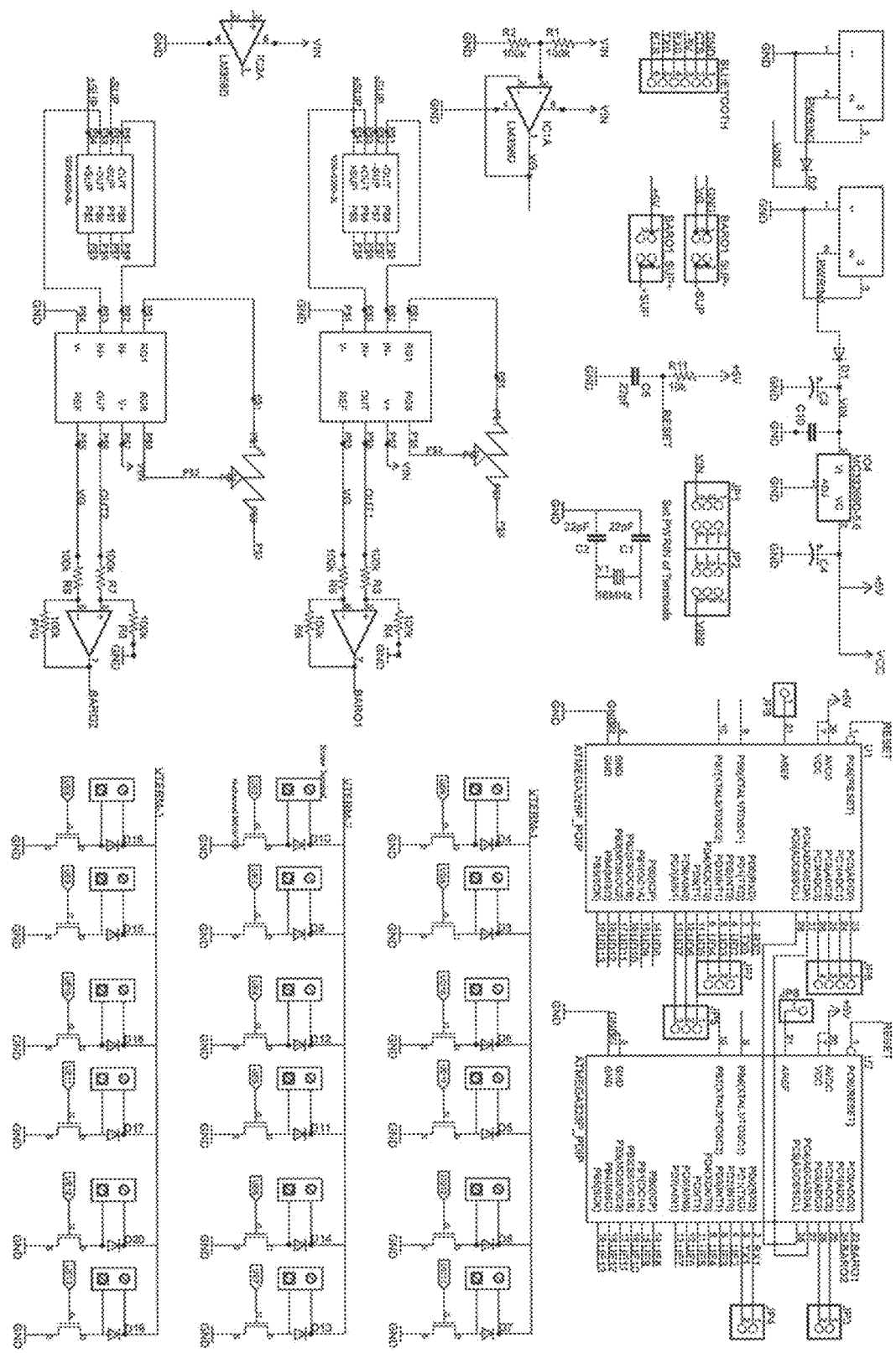

FIG. 21 illustrates an example PCB design.

DETAILED DESCRIPTION

Aspects of the disclosure are directed to handheld systems including multiple pressure sources, and method of use thereof. In some embodiments, the handheld systems include microfluidic components/subsystems having multiple pressure requirements that can be addressed via multiple pressure sources of the handheld systems.

In some embodiments, a handheld system includes a reference pressure source configured to generate a reference pressure. The handheld system also includes a primary pressure source coupled to the reference pressure source. The primary pressure source is configured to generate a primary pressure in a primary pressure range. The primary pressure is less than the reference pressure, and the primary pressure is induced by the reference pressure source. The handheld system also includes a secondary pressure source coupled to the primary pressure source. The secondary pressure source is configured to generate a secondary pressure in a secondary pressure range. The secondary pressure is less than the primary pressure, and the secondary pressure is induced by the primary pressure source.

In some embodiments, a handheld system includes a primary pressure source configured to generate a primary pressure in a primary pressure range. The reference pressure is induced by a reference pressure source. The handheld system also includes secondary pressure sources directly or indirectly coupled to the primary pressure source. Each secondary pressure source is configured to generate a secondary pressure in a second pressure range. Each secondary pressure is less than the primary pressure, and the secondary pressure is induced directly or indirectly by the primary pressure source. At least one secondary pressure source has a secondary pressure directly induced by the primary pressure source, and is directly coupled to the primary pressure source.

In some embodiments, a method includes operating a reference pressure source to induce, in a primary pressure source coupled to the reference pressure source, a primary pressure in a primary pressure range. The method further includes operating a first valve and a second valve to induce, in a secondary pressure source coupled to the primary pressure source, a secondary pressure in a secondary pressure range. The first valve is configured to couple the primary pressure source to the secondary pressure source. The second valve is coupled to the secondary pressure source, and is configured to regulate pressure in the secondary pressure source. The method further includes receiving an indication of pressure in the secondary pressure source. The method further includes, when the pressure in the secondary pressure source is outside the secondary pressure range, controlling operation of one or more of the first valve, the second valve, the reference pressure source, the primary pressure source, and the secondary pressure source to return pressure in the secondary pressure source to within the secondary pressure range.

In some embodiments, a handheld automated fluid handling system includes a pneumatic system capable of generating multiple pressure sources of different levels. The fluid handling system also includes one or more microfluidic chips, each microfluidic chip optionally including on-chip elastomeric valves. The fluid handling system also includes one or more pressure sensors, control electronics, a wireless communication module, and a control console.

Figure 1:
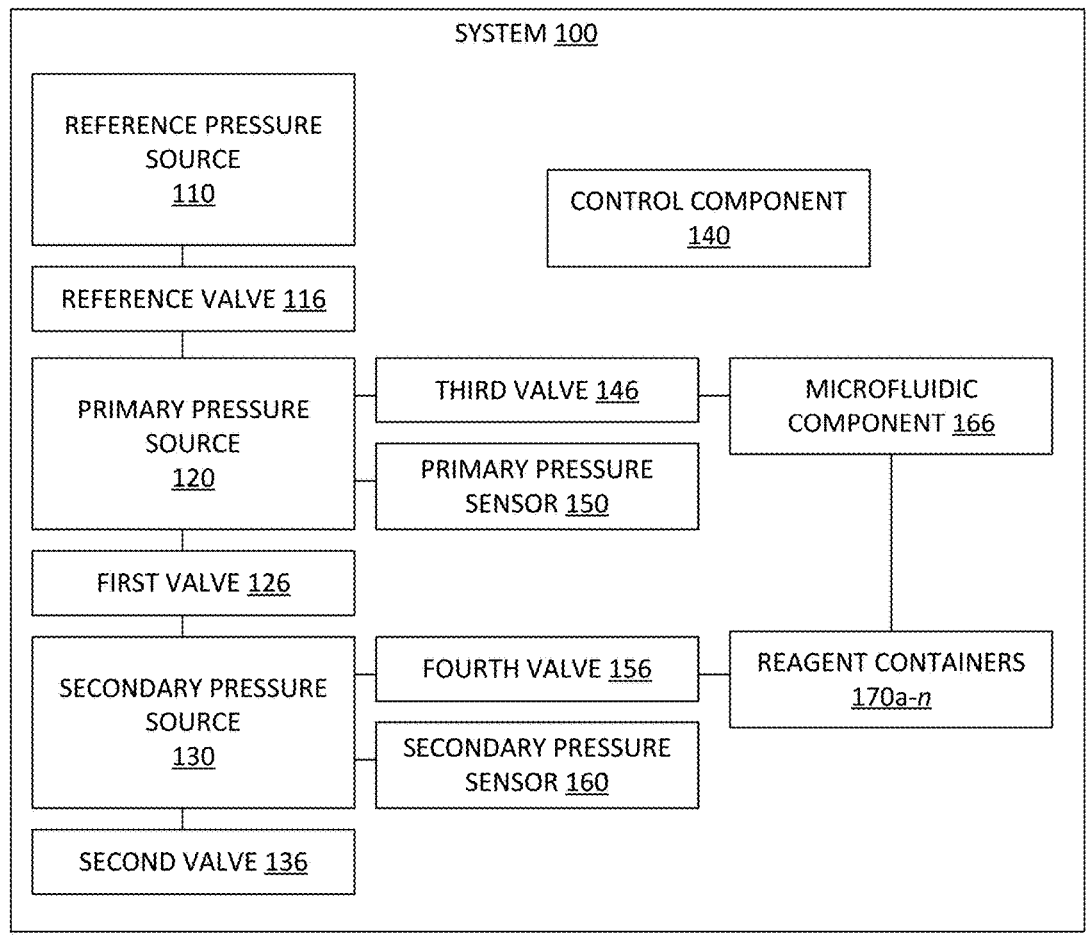
FIG. 1 illustrates a handheld system, according to an embodiment.

FIG. 1 illustrates a handheld system 100 having multiple pressure sources. In some embodiments, the system 100 is a lab-on-a-chip system including integrated pressure sources (and associated pneumatic components), and further including, but not limited to, at least one of the following capabilities: reagent handling (e.g., one or more reagent containers), sample handling (e.g., microfluidic cell culture systems, microfluidic cell sorting systems, and/or the like), power supply/generation (e.g., port for power input, integrated battery, and/or the like), system control (e.g., a processor/microprocessor, a memory, electrical and pneumatic communication lines, and/or the like), communication (e.g., wired communication, wireless communications such as via Bluetooth), and/or the like. As illustrated in FIG. 1, the system 100 can include a control component 140 (described in greater detail later) configured for controlling operation of the system 100.

The system 100, in the embodiment illustrated in FIG. 1, includes a reference pressure source 110, a primary pressure source 120, and a secondary pressure source 130. Each of the pressure sources 110, 120, 130 can independently be any suitable source configured for microfluidic flow control such as, for example, a pump, a pressure reservoir, a pressure tank, and/or the like. In this manner, the pressure sources 110, 120, 130 can independently be a direct source of pressure, such as a gas and/or liquid pump, or an indirect source of pressure, such as a pressure reservoir. In some embodiments, the reference pressure source 110 is a reference pump, and the pressure sources 120, 130 are pressure reservoirs. It is understood that while the pressure sources 110, 120, 130 are illustrated here as in a linear arrangement for simplicity, multiple numbers of each pressure source can exist, one of the pressure sources 110, 120, 130 can be connected to more than one pressure sources upstream and/or downstream, and/or the like. For example, the system 100 can include multiple reference pressure sources, each coupled to one or more primary pressure sources downstream. As another example, a single primary pressure source can be coupled to multiple secondary pressure sources, operating in parallel. As yet another example, additional pressure sources (not shown) may exist downstream of the secondary pressure sources.

In some embodiments, the reference pressure source 110 is configured to generate a reference pressure. In some embodiments, the reference pressure source 110 includes one or more of the following: a DC diaphragm pump, DC brushless pump, a valve, and a gas source. In some embodiments, the reference pressure source 110 is a positive pressure source, while in other embodiments, the reference pressure source can be a negative pressure source. The term "positive pressure" can mean any pressure value/range equal to or above a reference pressure (e.g., equal to or above atmospheric pressure, equal to or above atmospheric pressure, and/or the like), and the term "negative pressure" can mean any pressure value/range below the reference pressure (e.g., below atmospheric pressure, below atmospheric pressure, and/or the like).

In some embodiments, additional reference pressure sources can be included in the system 100, and coupled to the primary pressure source 120. For example, the system 100 can include the reference pressure source 110 coupled to the primary pressure source 120 as a positive pressure source, and can include a second reference pressure source (not shown) coupled to the primary pressure source 120 as a negative pressure source.

In some embodiments, at least one of the reference pressure source 110, the primary pressure source 120, and the secondary pressure source 130 can include a pressure reservoir. A pressure reservoir can be any suitable component that has a fixed or adjustable volume. Examples of suitable pressure reservoirs can include, but are not limited to, tanks, segments of tubing between two or more ports, a reservoir "cavity" built into a microfluidic component, and/or the like.

In some embodiments, the pressure reservoir can include one or more pressure input ports, and one or more pressure output ports. In some embodiments, the pressure reservoir can further include one or more pressure release ports configured to reduce a pressure differential between the pressure reservoir and ambient pressure outside the pressure reservoir. In some embodiments, at least one of the ports of the pressure reservoir includes a solenoid valve. In some embodiments, the solenoid valve can be a normally closed solenoid valve.

When the reference pressure source 110 is a negative pressure source, or is configured as a negative pressure source, in some embodiments (not shown in FIG. 1), the reference pressure source can include a pump and a negative pressure reservoir. The output of the negative pressure reservoir can then be coupled to the primary pressure source 120 to provide a source of negative pressure.

In some embodiments, the reference pressure source 110 is a pressure pump, the primary pressure source 120 is a primary reservoir coupled to the pressure pump, and the secondary pressure source 130 is a secondary reservoir coupled to the primary reservoir.

In some embodiments, the primary pressure source 120 is coupled to the reference pressure source 110, and is configured to generate a primary pressure. In some embodiments, the primary pressure is any suitable/desirable pressure within a primary pressure range. In some embodiments, the primary pressure is induced by the reference pressure source 110. In some embodiments, the primary pressure is less than the reference pressure (e.g., when the reference pressure source 120 is a positive pressure source), while in other embodiments, the primary pressure is more than the reference pressure (e.g., when the reference pressure source 120 is a negative pressure source). In some embodiments, the reference pressure source 110 is configured to maintain the primary pressure within the primary pressure range. In some embodiments, the primary pressure source 120 is a primary reservoir having a primary reservoir volume.

In some embodiments, the secondary pressure source 130 is coupled to the primary pressure source 120, and is configured to generate a secondary pressure in a secondary pressure range. In some embodiments, the secondary pressure is induced by the primary pressure source. In some embodiments, the secondary pressure is less than the primary pressure. In some embodiments, the secondary pressure source 130 is a secondary reservoir having a secondary reservoir volume. In some embodiments, the secondary reservoir volume is greater than the primary reservoir volume.

Referring again to FIG. 1, in some embodiments, the system 100 includes a reference valve 116 configured to couple the reference pressure source 110 to the primary pressure source 120. In some embodiments, the reference valve 116 includes a solenoid valve.

In some embodiments, the system 100 includes a first valve 126 configured to couple the primary pressure source 120 to the secondary pressure source 130. In some embodiments, the first valve 126 includes a normally closed two-way solenoid valve.

In some embodiments, the system 100 further includes a second valve 136 coupled to the secondary pressure source 130. In some embodiments, the second valve 136 is configured to regulate the secondary pressure. In some embodiments, the second valve 136 includes a normally closed two-way solenoid valve. In some embodiments, the second valve 136 and the first valve 126 are configured to maintain the secondary pressure within the secondary pressure range.

In some embodiments, the system 100 further includes a third valve 146 configured to couple the primary pressure source 120 to a primary pressure outlet for providing pressure in the primary pressure range. In some embodiments, the system 100 further includes a fourth valve 156 configured to couple the secondary pressure source 130 to a secondary pressure outlet for providing pressure in the secondary pressure range. In some embodiments, at least one of the reference valve 116, the first valve 126, the second valve 136, the third valve or the fourth valve 156 includes a flow restrictor.

In some embodiments, the system 100 further includes a primary pressure sensor 150 coupled to the primary pressure source 120. The primary pressure sensor 150 is configured to sense pressure in the primary pressure source 120. In some embodiments, the reference pressure source 110 is configured to maintain the primary pressure within the primary pressure range based on feedback from the primary pressure sensor 150. In some embodiments, the first valve 126 includes a normally closed valve, and is configured to open when the secondary pressure falls below a lower bound of the secondary pressure range. In some embodiments, the lower bound of the secondary pressure range is about 0 pounds per square inch (psi), about 1 psi, about 2 psi, about 3 psi, about 4 psi, about 5 psi, including all values in between.

In some embodiments, the system 100 further includes a secondary pressure sensor 160 coupled to the secondary pressure source 130. The secondary pressure sensor 160 is configured to sense pressure in the secondary pressure source 130. In some embodiments, the second valve 136 and the first valve 136 are configured to maintain the secondary pressure within the secondary pressure range based on feedback from the secondary pressure sensor 160. In some embodiments, the second valve 136 includes a normally closed valve, and is configured to open when the secondary pressure exceeds an upper bound of the secondary pressure range. In some embodiments, the upper bound of the secondary pressure range is about 1 psi, about 2 psi, about 3 psi, about 4 psi, about 5 psi, about 6 psi, about 7 psi, about 8 psi, about 9 psi, about 10 psi, including all values in between.

In some embodiments, at least one of the sensors 150, 160 can be inside the reservoir volume of the primary pressure source 120, secondary pressure source 130, respectively.

In some embodiments, the primary reservoir volume of the primary pressure source 120 is defined by the reference valve 116, the primary pressure sensor 150, the first valve 126, and the third valve 146. In some embodiments, the primary reservoir volume is about 3 mL, about 4 mL, about 5 mL, about 6 mL, about 7 mL, about 8 mL, about 9 mL, about 10 mL, including all values in between. In some embodiments, the secondary reservoir volume is defined by the first valve 126, the secondary pressure sensor 160, the second valve 136, and the fourth valve 156. In some embodiments, the secondary reservoir volume is about 10 mL, about 12 mL, about 14 mL, about 16 mL, about 18 mL, about 20 mL, about 22 mL, about 25 mL, including all values in between.

The control component 140 can be operably connected (connections not shown for simplicity) to any of the components of the system 100, including at least one of the reference pressure source 110, the primary pressure source 120, the secondary pressure source 130, the reference valve 116, the first valve 126, the second valve 136, the third valve 146, the fourth valve 156, the primary pressure sensor 150, or the secondary pressure sensor 160. In some embodiments, the control component 140 is configured to maintain pressure in the primary pressure source 120 in the first pressure range, and to maintain pressure in the secondary pressure source 130 in the second pressure range. In some embodiments, the control component 140 includes a wireless controller and/or interface, permitting a user of the system 100 to control operation of the system from a remote location such as, for example, a laptop, a tablet, a smartphone, and/or the like. In some embodiments, the control component 140 includes an electronic printed circuit board (PCB) having one or more microcontrollers configured to perform the functions of the control component 140 described herein.

It is understood that while the control component 140 is illustrated as a single component, aspects of the structure and/or functionality can be embodied in subcomponents that are within and/or otherwise associated with other components. For example, in some embodiments, when any of the pressure sources 110, 120, 130 includes a pressure reservoir, aspects of the control component (e.g., pressure monitoring control, data communications, and/or the like) may be implemented in a control unit (not shown) within the volume of the pressure reservoir. As another example, when the sensor 150 is inside the volume of the pressure source 120, a control unit inside the primary pressure source 120 can monitor the sensor 150, and can communicate an indication of the sensed pressure to the control component 140, can control the ports of the pressure reservoir to change the pressure inside the primary pressure source 120, and/or the like.

In some embodiments, the control component 140 is coupled to, and configured for control of the reference pressure source 110, the first valve 126, and the second valve 136. In such embodiments, the control component 140 can be configured to maintain the primary pressure in the primary pressure range, and to maintain the secondary pressure in the secondary pressure range.

In some embodiments, the control component 140 can be further configured to run and/or operate the reference pressure source 110 when pressure in the primary pressure source 120 falls below a lower bound of the primary pressure range. In some embodiments, the lower bound of the primary pressure range is about 7 psi, about 8 psi, about 9 psi, about 10 psi, about 12 psi, about 14 psi, including all values in between. In some embodiments, an upper bound of the primary pressure range is about 10 psi, about 12 psi, about 14 psi, about 16 psi, about 18 psi, about 20 psi, about 22 psi, about 24 psi, about 28 psi, about 30 psi, including all values in between.

The control component 140 can be further configured to open the first valve 126 when pressure in the secondary pressure source 130 falls below a lower bound of the secondary pressure range. The control component 140 can be further configured to open the second valve 136 when pressure in the secondary pressure source 130 rises above an upper bound of the secondary pressure range.

In some embodiments, the system 100 further includes a microfluidic component 166 operably coupled to the control component 140 (not shown). In some embodiments, the microfluidic component 166 is further coupled to the primary pressure source and to the secondary pressure source. In some embodiments, the microfluidic component 166 can be fabricated at least in part from an elastomeric material, such as, for example, Polydimethylsiloxane (PDMS).

In some embodiments, the system 100 further includes a microfluidic component 166 operably coupled to the control component 140 (not shown). In some embodiments, the microfluidic component 166 is further coupled to the primary pressure source and to the secondary pressure source. In some embodiments, the microfluidic component 166 can be fabricated at least in part from an elastomeric material, such as Polydimethylsiloxane (PDMS). In some embodiments, the microfluidic component 166 can include, but is not limited to, an enzyme linked immunosorbent assay (ELISA) device, a fluorescence immunoassay device, a polymerase chain reaction (PCR) device, a fluorescence in situ hybridization (FISH) device, a flow cytometry device, a nucleic acid sequencing device, or a quality testing device.

In some embodiments, the system 100 further includes one or more reagent containers 170a-n configured to hold one or more reagents for use by the system for sample processing. The reagent containers 170a-n can be fluidly coupled to the microfluidic component 166 for supplying, drawing and/or otherwise circulating reagents. Each reagent containers 170a-n can also be independently coupled to one or more of the pressure sources 110, 120, 130 for driving the circulation of reagents. In this manner, since each of the pressure sources 110, 120, 130 generates a different pressure/pressure range, an appropriate pressure input can be applied to the reagent containers 170a-n to conduct sample processing as necessary.

In some embodiments, the third valve 146 is configured to couple the primary pressure source 120 to the microfluidic component 166, such as via one or more primary pressure outlets, for controlling operation of the microfluidic component. In some embodiments, the fourth valve 156 is configured to couple the secondary pressure source 130 to the microfluidic component 166, such as via one or more secondary pressure outlets, for controlling reagent input to the microfluidic component. In some embodiments, the control component 140 is configured to maintain pressure in the primary pressure source 120 in the primary pressure range for controlling operation of the microfluidic component 160, and is further configured to maintain the pressure in the secondary pressure source 130 in the secondary pressure range for controlling reagent input to the microfluidic component.

In some embodiments, the control component 140 is configured to control reagent input to the microfluidic component by controlling one or more secondary outlets of the secondary pressure source 130. The one or more secondary outlets are configured to be coupled to one or more of the reagent containers 170*a-n* that supply reagents to the microfluidic component 166.

Figure 2:
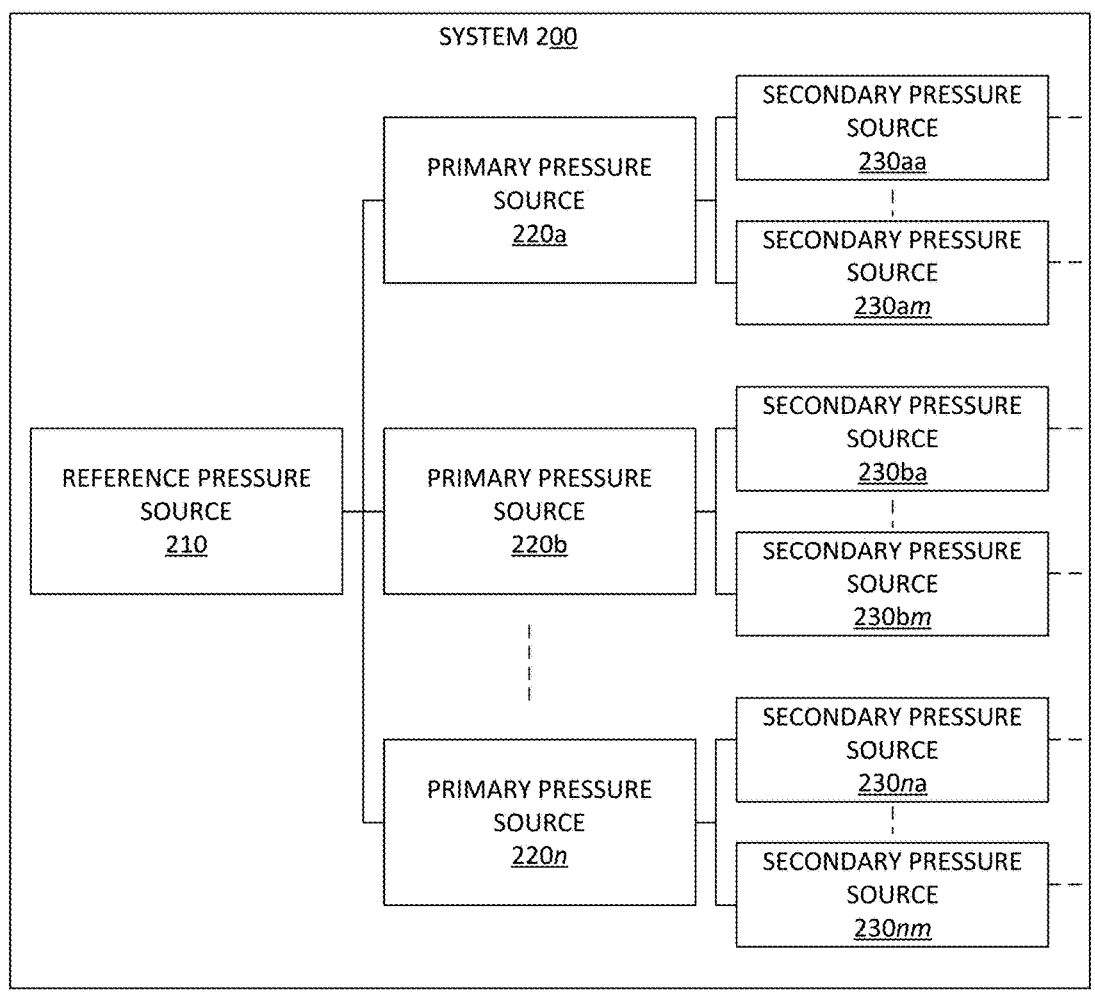
FIG. 2 illustrates the pressure components of a handheld system, according to another embodiment.

FIG. 2 illustrates another arrangement of the various pressure sources of FIG. 1 in a system 200, according to embodiments. Such an arrangement of pressure sources can be partly or wholly included within the handheld system 100 of FIG. 1. Unless explicitly indicated otherwise, similarly named and/or numbered components can be structurally and/or functionally similar to those in FIG. 1. For example, the reference pressure source 210 can be similar to the reference pressure source 110.

While not illustrated in FIG. 2, it is understood that each pressure source can be associated with other components as illustrated for its similarly named/numbered pressure source in FIG. 1. For example, the reference pressure source 210 can be coupled to a control component and a reference pressure valve; any or all of the primary pressure sources 220*a-*220*n* can be individually coupled to a control component, a reference pressure valve, a first valve, a third valve, and a primary pressure sensor; any or all of the secondary pressure sources 230*aa-*230*an* . . . 230*na-*230*nm* can be individually coupled to a control component, a first valve, a second valve, a fourth valve, and a secondary pressure sensor; and so on. Additional pressure sources (not shown) can be coupled to the secondary pressure sources 230*aa-*230*an* . . . 230*na-*230*nm*, and can also be regarded as secondary pressure sources that are indirectly coupled to the primary pressure sources 220*a-*220*n* via the secondary pressure sources 230*aa-*230*an* . . . 230*na-*230*nm*.

FIG. 2 illustrates a handheld system 200 including a reference pressure source 210 operably coupled to multiple primary pressure sources 220*a-*220*n* operably coupled to the reference pressure source. Each primary pressure source 220*a-*220*n* is configured to generate a primary pressure in a primary pressure range, the reference pressure induced by a reference pressure source. The primary pressure generated by any of the primary pressure sources 220*a-*220*n* (e.g., the primary pressure source 220*a*) can be substantially similar, overlapping, or exclusive with respect to any of the other primary pressure sources.

FIG. 2 illustrates a reference pressure source 210 operably coupled to multiple primary pressure sources 220*a-*220*n* operably coupled to the reference pressure source. Each primary pressure source 220*a-*220*n* is configured to generate a primary pressure in a primary pressure range, the reference pressure induced by the reference pressure source. The primary pressure generated by any of the primary pressure sources 220*a-*220*n* (e.g., the primary pressure source 220*a*) can be substantially similar, overlapping, or exclusive with respect to any of the other primary pressure sources.

Described here with respect to the primary pressure source 220*a* for simplicity, FIG. 2 also illustrates multiple secondary pressure sources 230*aa-*230*am* coupled to the primary pressure source 220*a*. Each secondary pressure source 230*aa-*230*am* is configured to generate a secondary pressure in a second pressure range. Each secondary pressure of the secondary pressure sources 230*aa-*230*am* is less than the primary pressure of the primary pressure source 220*a*. The secondary pressure is induced directly or indirectly by the primary pressure source 220*a*. In some embodiments, at least one secondary pressure source (e.g., the secondary pressure source 230*aa*) has a secondary pressure directly induced by its primary pressure source 220*a*.

In some embodiments, at least one secondary pressure source (e.g., the secondary pressure source 230*aa*) is arranged in a cascade with respect to at least one other secondary pressure source (e.g., another secondary pressure source downstream of the secondary pressure source 230*aa*, not shown) of the plurality of secondary pressure sources.

As illustrated in FIG. 2, in some embodiments, at least one secondary pressure source (e.g., the secondary pressure source 230*aa*) is arranged in parallel with respect to at least one other secondary pressure source (e.g., the secondary pressure source 230*an*, or the secondary pressure source 230*ba*) of the plurality of secondary pressure sources.

In some embodiments, each primary pressure source (e.g., the primary pressure source 220*a*) is associated with a primary reservoir volume, and at least one secondary pressure source (e.g., the secondary pressure source 230*aa*) is associated with a second reservoir volume. In some embodiments, the second reservoir volume greater than the first reservoir volume. Described with reference to the primary pressure source 220*a*, in some embodiments, the system 200 can further include a first valve (e.g., similar to the first valve 126) configured to couple the primary pressure source 220*a* to at least one of the secondary pressure sources 230*aa-*230*am*, such as the secondary pressure sources 230*aa*, for example. In some embodiments, the system 200 can include multiple first valves. Each first valve can be configured to couple the primary pressure source 220*a* to a corresponding secondary pressure source of the secondary pressure sources 230*aa-*230*am*.

In some embodiments, the system 200 can further include a second valve (e.g., similar to the second valve 136) coupled to the secondary pressure source 230*aa*. The second valve is configured to regulate the secondary pressure, to couple the secondary pressure source 230*aa* to another secondary pressure source (not shown), or both. In some embodiments, the system 200 can further include multiple second valves coupled to multiple secondary pressure sources. Each second valve can be configured to regulate pressure in a preceding and/or upstream secondary pressure source, or to couple two secondary pressure sources, or both.

In some embodiments, the system 200 can further include a pressure outlet coupled to at least one of the primary pressure sources 220*a-*220*n* or the secondary pressure sources 230*aa-*230*am*. In some embodiments, system 200 can include at least one primary pressure outlet coupled to one of the primary pressure sources (e.g., the primary pressure source 220*a*), and at least one secondary pressure outlet coupled to one of the corresponding secondary pressure sources (e.g., the secondary pressure source 230*aa*).

In some embodiments, the system 200 can further include a microfluidic component (e.g., similar to the microfluidic component 166) coupled to one or more of the primary pressure sources 220*a-*220*n*, and to one or more of the secondary pressure sources 230*aa-*230*an* . . . 230*na-*230*nm*. In some embodiments, the system 200 can further include a control component (e.g., similar to the control component 140) configured to maintain the primary pressure in the primary pressure source(s) coupled to the microfluidic component (e.g., in the primary pressure source 220*a*) in the primary pressure range for controlling operation of the microfluidic component. In some embodiments, the control component can be further configured to maintain the secondary pressure in the secondary pressure source(s) coupled to the microfluidic component (e.g., in the secondary pressure source 230aa) in the second pressure range for controlling reagent input to the microfluidic component.

Figure 3:
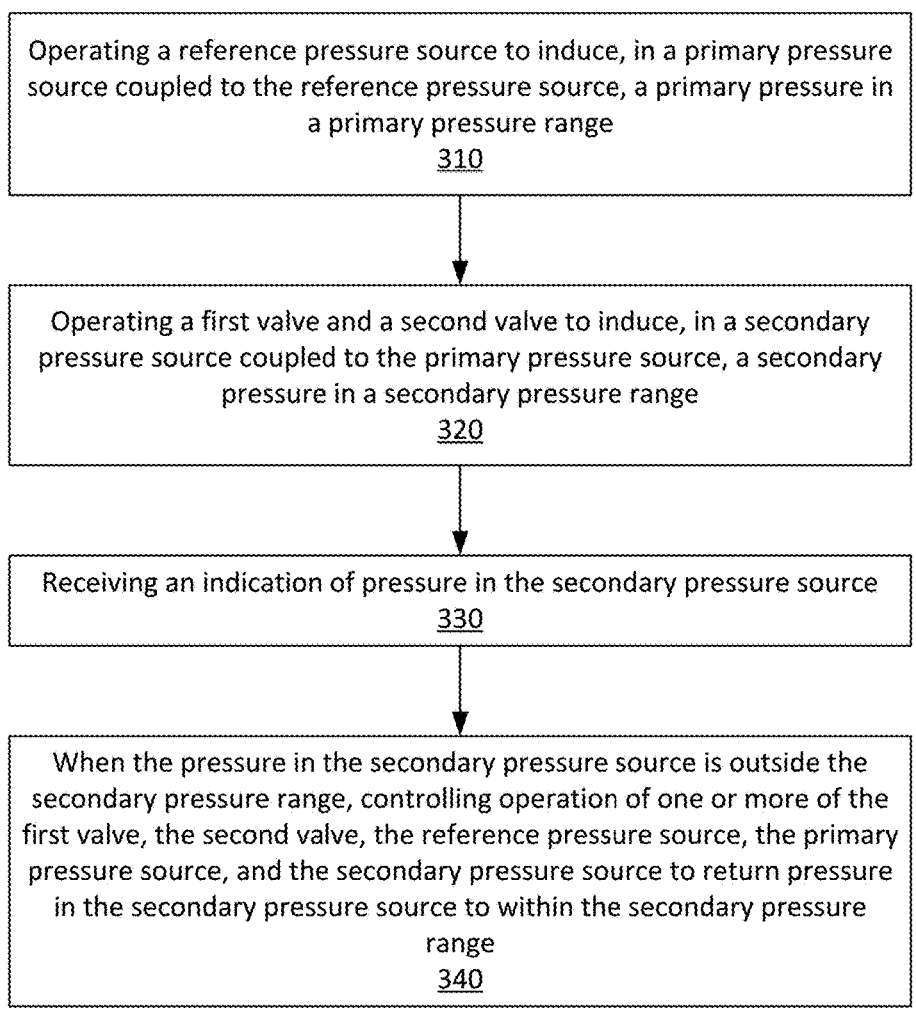
FIG. 3 illustrates a method of a handheld system, according to an embodiment.

FIG. 3 illustrates a method 300, such as for controlling operation of the system 100 and/or the system 200. Explained herein with reference to the system 100 of FIG. 1, at 310, in some embodiments, the method 300 can be executed by a controller of a handheld system, such as, for example, the control component 140 of the system 100. In some embodiments, the controller includes one or more processors configured to execute the method 300. In some embodiments, the controller includes a memory storing computer executable instructions (e.g., executable by a processor of the controller) for executing the method 300.

At 310, the method 300 includes operating a reference pressure source (e.g., the reference pressure source 110) to induce, in a primary pressure source (e.g., the primary pressure source 120) coupled to the reference pressure source, a primary pressure in a primary pressure range.

At 320, the method 300 includes operating a first valve (e.g., the first valve 126) and a second valve (e.g., the second valve 136) to induce, in a secondary pressure source (e.g., the secondary pressure source 130) coupled to the primary pressure source, a secondary pressure in a secondary pressure range. The first valve is configured to couple the primary pressure source to the secondary pressure source. The second valve is coupled to the secondary pressure source and configured to regulate pressure in the secondary pressure source.

At 330, the method 300 includes receiving an indication of pressure in the secondary pressure source, such as from, for example, a pressure sensor (e.g., the secondary pressure sensor 160).

At 340, the method 300 includes, when the pressure in the secondary pressure source is outside the secondary pressure range, controlling operation of one or more of the first valve, the second valve, the reference pressure source, the primary pressure source, and the secondary pressure source to return pressure in the secondary pressure source to within the secondary pressure range.

In some embodiments, when the pressure in the secondary pressure source is above an upper bound of the secondary pressure range, controlling the operation can further include operating the second valve to release pressure from the secondary pressure source, and operating the first valve or the reference pressure source, or both, to reduce the inducement of pressure in the secondary pressure source. In some embodiments, when the pressure in the secondary pressure source is above an upper bound of the secondary pressure range, the controlling the operation can further include operating the second valve to reduce pressure in the secondary pressure source, and controlling a secondary reservoir volume associated with the secondary pressure source. In some embodiments, when the pressure in the secondary pressure source is above an upper bound of the secondary pressure range, the controlling the operation can further include operating the reference pressure source to reduce the inducement of pressure in the secondary pressure source, increasing a secondary reservoir volume associated with the secondary pressure source.

In some embodiments, when the pressure in the secondary pressure source is below a lower bound of the secondary pressure range, controlling the operation can further include operating the second valve to retain pressure in the secondary pressure source, and operating the first valve or the reference pressure source, or both, to increase the inducement of pressure in the secondary pressure source.

In some embodiments, the method 300 can further include receiving an indication of pressure in the primary pressure source, such as from, for example, the primary pressure sensor 150. In such embodiments, the method 300 can further include, when the pressure in the primary pressure source is outside the primary pressure range, controlling operation of the first valve, the reference pressure source, or both, to return pressure in the primary pressure source to within the primary pressure range.

In some embodiments, the method 300 can further include operating a third valve (e.g., the third valve 146) configured to couple the primary pressure source to a primary pressure outlet. In some embodiments, the primary pressure outlet is operably coupled to a microfluidic component (e.g., the microfluidic component 166), and the method 300 can further include operating the third valve to couple the primary pressure source to the primary pressure outlet for controlling operation of a microfluidic component. In some embodiments, the method 300 can further include operating a set of third valves configured to couple the primary pressure source to a set of primary pressure outlets for controlling operation of a microfluidic component.

In some embodiments, the method 300 can further include operating a fourth valve (e.g., the fourth valve 156) configured to couple the secondary pressure source to a secondary pressure outlet. In some embodiments, the secondary pressure outlet is operably coupled to reagent containers for supplying one or more reagents to the microfluidic component, and the method 300 can further include operating the fourth valve configured to couple the secondary pressure source to the secondary pressure outlet for controlling reagent input to the microfluidic component. In some embodiments, the method 300 can further include operating a set of fourth valves configured to couple the secondary pressure source to a set of secondary pressure outlets for controlling reagent input to the microfluidic component.

Example 1

Figure 4:
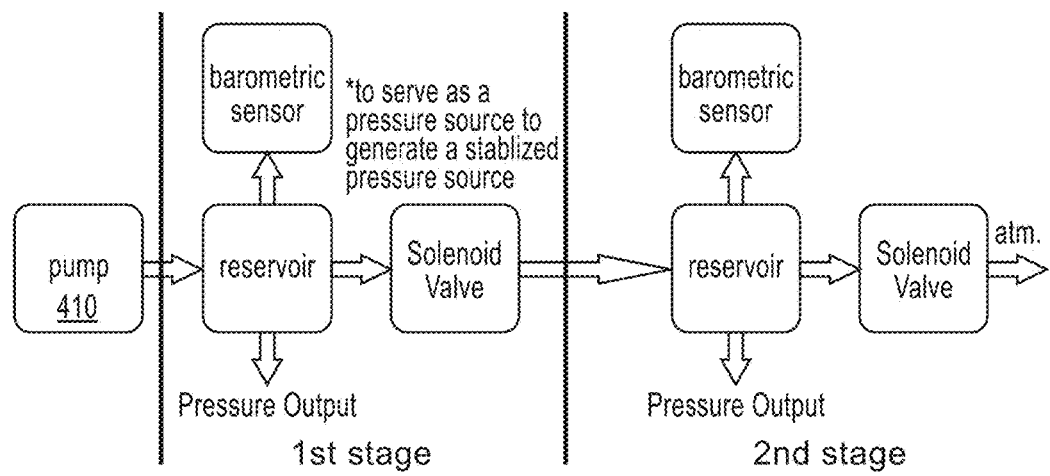
FIG. 4 is an example pneumatic system.

FIG. 4 illustrates a pneumatic subsystem, such as can be implemented within the system 100 and/or the system 200. This pneumatic subsystem uses one air pump 410 and numerous solenoid valves to generate multiple stabilized pressure sources ("$1^{st}$ stage" and "$2^{nd}$ stage" pressure sources) of different levels/stages, whose maximum pressure output values are limited by the power of the air pump. Microcontrollers and load switch circuits (not shown) are used to control the pump 410 and solenoid valves. The pressure level in each stage is monitored by a barometric sensor, which transduces air pressure level to electrical signal, in real-time. The electrical signal is acquired by a microcontroller with analog-to-digital (ADC) converter(s) with feedback control. This pneumatic subsystem is controlled by multiple microcontrollers, and additional microcontrollers can be added as necessary.

The 1st stage pressure source (e.g., similar to the primary pressure source 120), which is relatively unstable, is directly generated by the pump 410 (e.g., similar to the reference pressure source 110), while the $2^{nd}$ stage pressure source (e.g., similar to the secondary pressure source 130), which is relatively stable, is generated from the $1^{st}$ stage pressure source. In addition, as illustrated in FIG. 4, a dedicated solenoid valve is used to release the air pressure in the second stage pressure source for feedback control purposes.

Example 2

Figure 5:
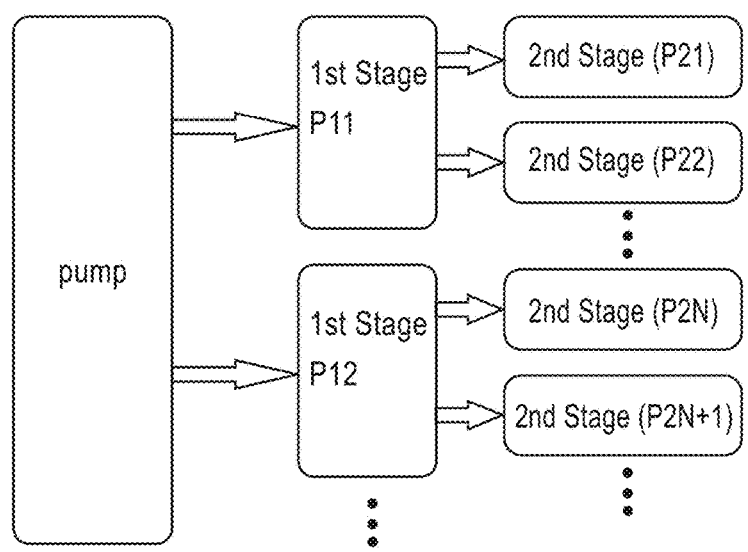
FIG. 5 is another example pneumatic system.

FIG. 5 illustrates the pneumatic subsystem of FIG. 4 extended to a pneumatic subsystem with many pressure sources. Each pressure source is constructed in a manner similar to described in FIG. 4. The pressure level in each pressure source can be stabilized by feedback control.

Example 3

Figure 6:
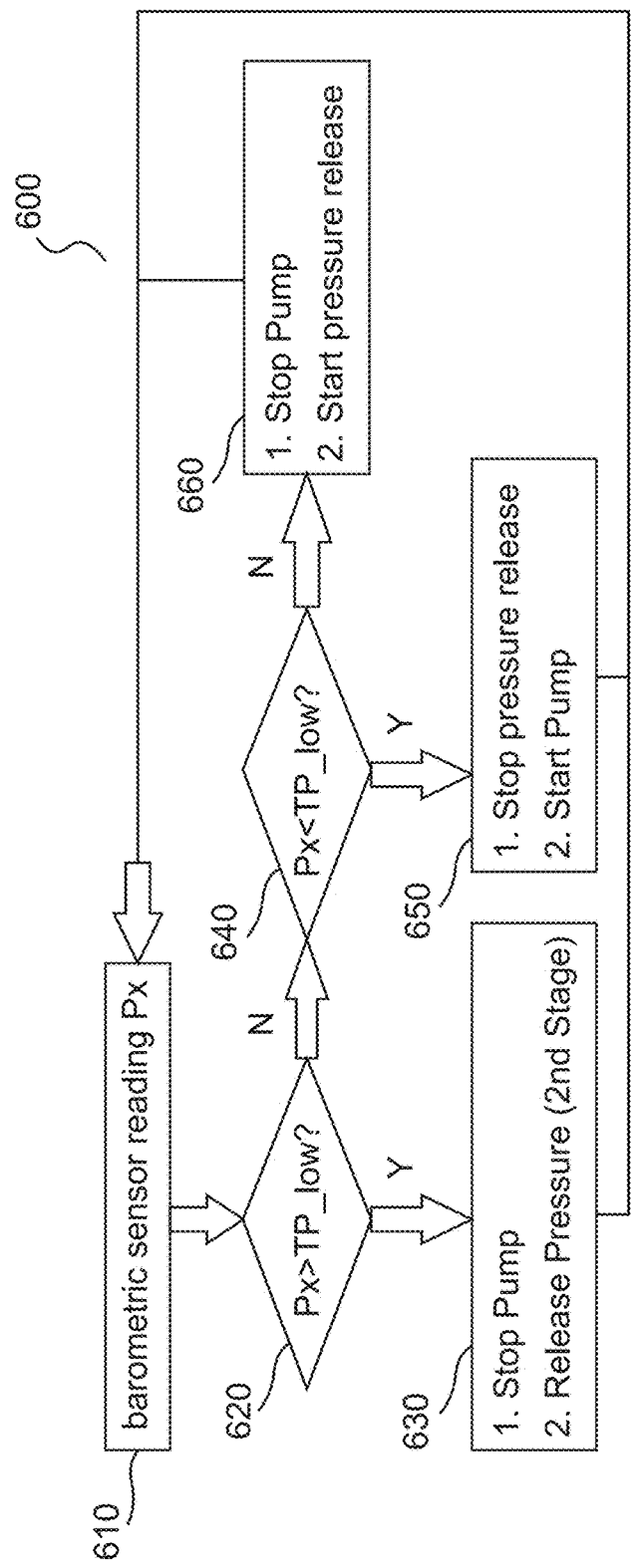
FIG. 6 is an example method of the pneumatic system of FIG. 4.

FIG. 6 illustrates an example method 600 of feedback pressure control, such as can be implemented by a control component (e.g., the control component 140). At 610, a sensor reading Px is obtained for a pressure source. At 620, a check is performed to see if Px>Upper Bound of Target Pressure (TP_up); if so, the pump/pressure source stops operating and a valve (e.g., one that vents to the atmosphere) can be actuated to decrease pressure at 630. If step 620 is not satisfied, then at 640, a check is performed to see if Px<Lower Bound of Target Pressure (TP_low); if so, at 650, any pressure release by the pressure source being monitored is stopped, a valve connecting the pressure source being monitored to an upstream pressure source is opened, and the upstream pump/pressure source is started. If none of 620 or 640 is true, then there is no need to modify pressure in the pressure source; accordingly, any pressure release by the pressure source being monitored is stopped, and the upstream pump/pressure source is stopped as well.

Example 4

Pressure release from a pressure source can be generally accomplished in at least two different ways. First, compressed air in the pressure source can be released to the ambient surroundings, which can be at atmospheric pressure, such as via a pressure vent port. The speed/rate of pressure release can be controlled by controlling the size of the pressure vent port. Second, the volume of the pressure source/reservoir can be expanded. The speed/rate of pressure release can be controlled by controlling the expanded volume size.

FIGS. 7A-7B illustrate an example 3-way solenoid valve in an OFF (FIG. 7A) and ON (FIG. 7B) configuration. When the normally close port is connected to a pressure reservoir, in the OFF configuration, the common port is in communication with the normally open port, which in turn can be in fluid communication with ambient surroundings. In the ON configuration, the normally close port is in communication with the volume of the common port, and the normally open port is cut off.

Figure 8A:
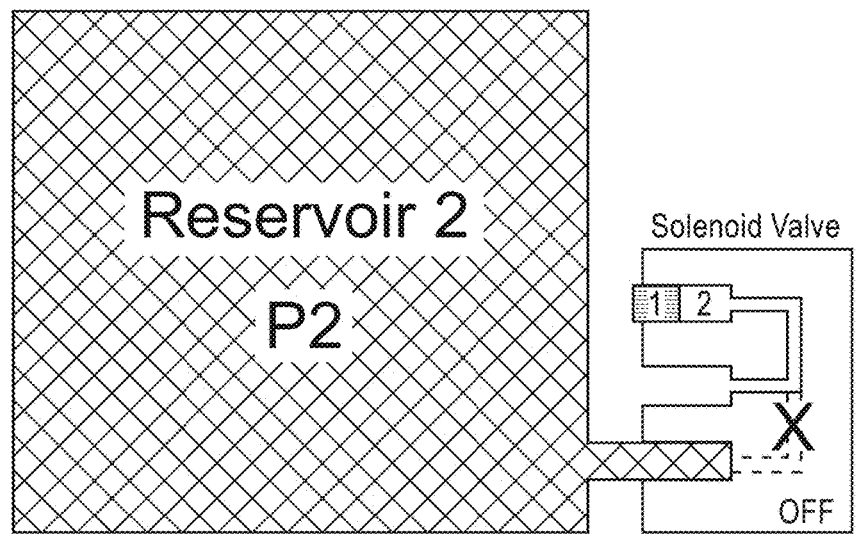
FIGS. 8A-8C are example illustrations of reducing pressure in a reservoir by increasing volume using the solenoid valve of FIGS. 7A-7B.
Figure 8B:
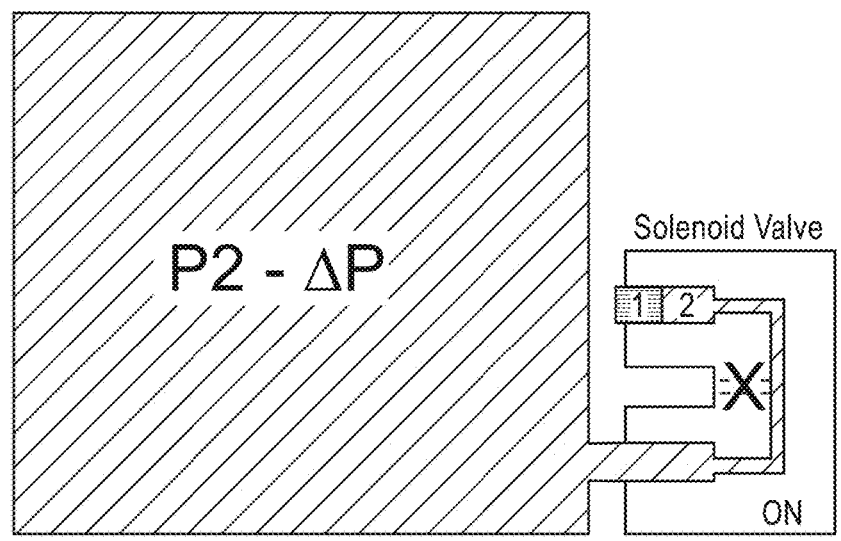
Figure 8C:
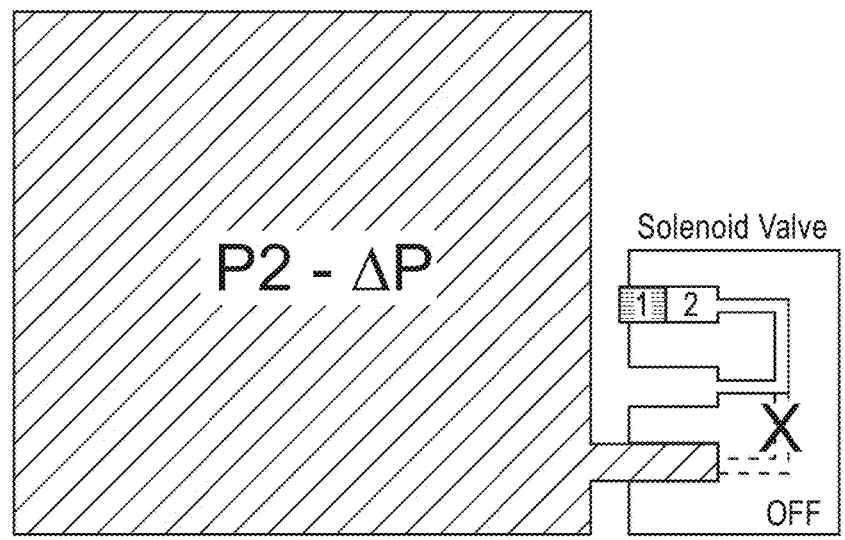

FIGS. 8A-8C illustrate an example embodiment of how pressure release in a pressure reservoir can be achieved by expansion. FIG. 8A illustrates a pressure reservoir with a pressure P2, coupled to the normally close port of a solenoid valve (e.g., the solenoid valve of FIGS. 7A-7B). The solenoid valve includes a small internal volume "2" formed by sealing the common port of the solenoid valve that, in the OFF configuration of the solenoid valve, is inaccessible to the volume of the pressure reservoir. FIG. 8B illustrates the ON configuration of the solenoid valve in which the internal volume "2" is continuous with the volume of the pressure reservoir, thereby increasing the volume of the pressure reservoir, and thereby reducing the pressure P2 to (P2-ΔP). Once the desired pressure P2-ΔP is accomplished, the solenoid valve reverts to the OFF configuration (see FIG. 8C).

In some cases, it takes about 10 ms for some solenoid valves (e.g., the Pneumadyne, S10MM-30-12-3) to be opened or closed completely, so the maximum frequency of the stepwise pressure releasing can be about 50 Hz in such cases. Still referring to FIGS. 8A-8C, the resolution of pressure release can be determined by the ratio of the volume of Reservoir 2 and the small internal volume of Valve 2 (i.e., the small internal volume "2" illustrated in FIGS. 8A-8C). This allows estimation of the small internal volume according to the Ideal Gas Law: PV=nRT. Assume that the volume of Reservoir 2 is $V_1$, and the small internal volume of Valve 2 is $V_2$. Compared to the volume of Reservoir 2 (16.2 mL), the small internal volume of Valve 2 is relatively small. So, the number of molecules inside the small internal volume can be ignored. Assume that temperature T is constant during our experiments, for every stepwise pressure release, the following applies: $P_1V_1=P_2(V_1+V_2)$. See Table 1.

TABLE 1

Stepwise pressure values

| Valve Toggle Times | Pressure in Reservoir 2 |
|---|---|
| 0 | $P_0$ |
| 1 | $P_1 = P_0\left(\dfrac{V_1}{V_1 + V_2}\right)$ |
| 2 | $P_2 = P_1\left(\dfrac{V_1}{V_1 + V_2}\right) = P_0\left(\dfrac{V_1}{V_1 + V_2}\right)^2$ |
| 3 | $P_3 = P_0\left(\dfrac{V_1}{V_1 + V_2}\right)^3$ |
| ... | ... |
| x | $P(x) = P_0\left(\dfrac{V_1}{V_1 + V_2}\right)^x$ |
| ... | ... |

Figure 8D:
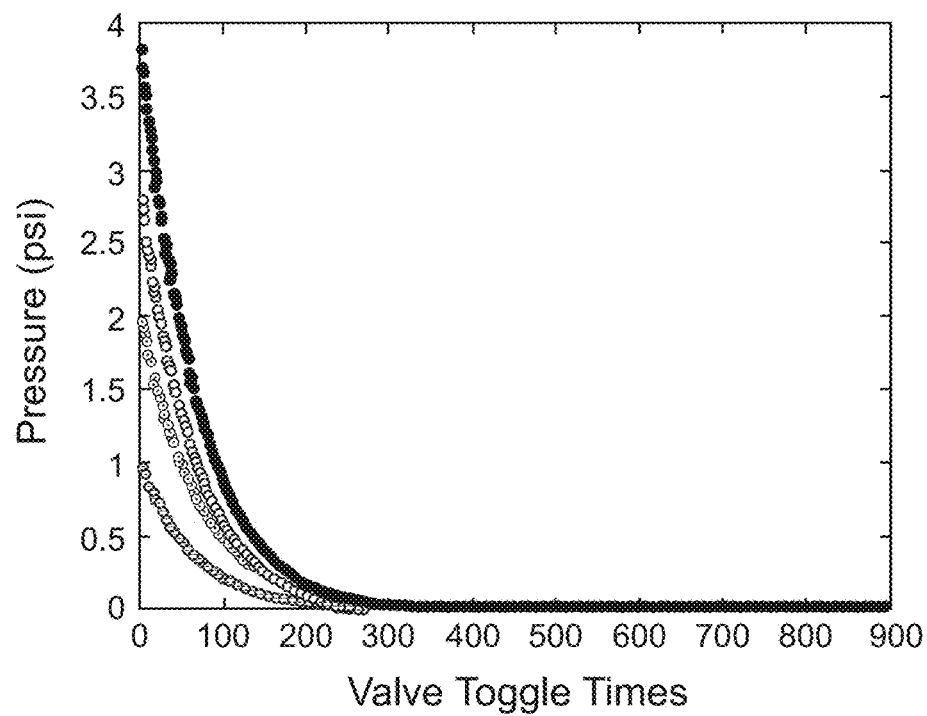
FIG. 8D and 8E illustrate the change in pressure as the solenoid vlave moves from the first configuration, as shown in FIG. 8A, to the second configuration, as shown in FIG. 8B, on linear and semi-log plots, respecctively.

FIG. 8D illustrates the stepwise pressure release data as an exponential function.

Figure 8E:
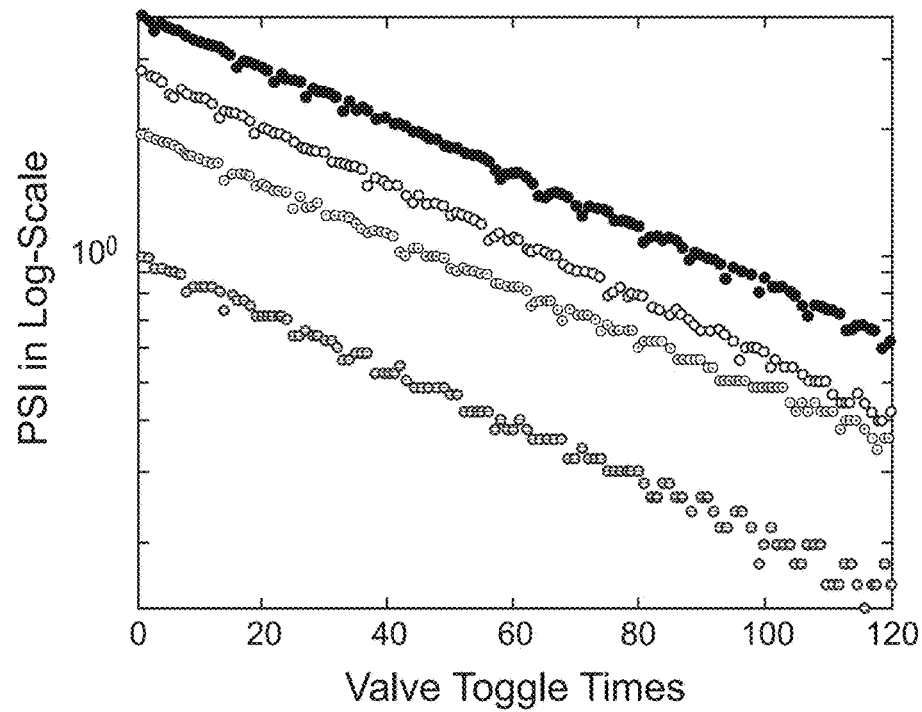

It is now possible to plot these data in semi-log graph and estimate the volume by straight line fitting (FIG. 8E). Table 2 lists estimated values of the small internal volume "2"

TABLE 2

| Data Series | Slope of Fitted Lines | Estimated $V_2$ (ml) |
|---|---|---|
| 1 | −0.015508 | 0.2532 |
| 2 | −0.01427 | 0.2328 |
| 3 | −0.016023 | 0.2617 |
| 4 | −0.015104 | 0.2465 |
| Average | | 0.2486 |

Therefore, the estimated small internal volume of "2" is about 250 μL. Systematic error may be estimated by substituting absolute pressure with gauge pressure.

Example 5

Figure 9A:
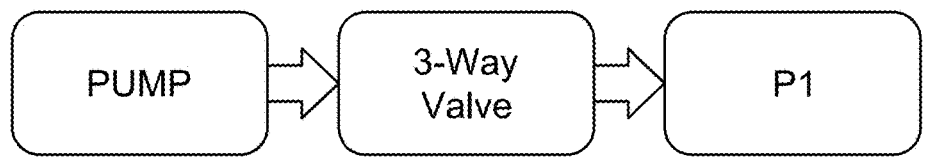
FIG. 9A is an example illustration of a 3-way valve interconnecting a pump and a pressure source.

FIG. 9A illustrates an example embodiment where a 3-way valve (e.g., similar to the reference valve 116) is used between the pump (e.g., similar to the reference pressure source 110) and a pressure source P1 (e.g., similar to the primary pressure source 120).

Figure 9B:
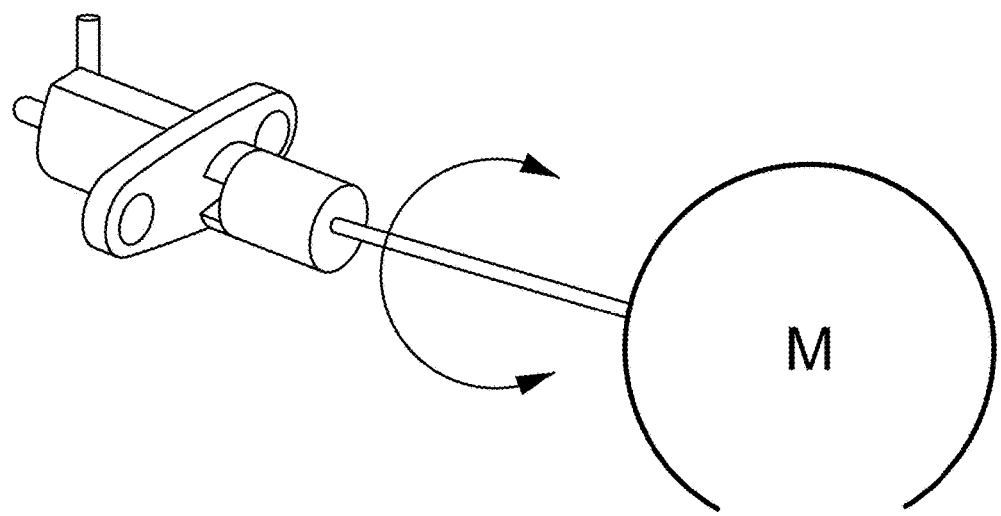
FIG. 9B is an example illustration of a needle restrictor usable as a valve.

Generally, miniature electromechanical pneumatic components M can also be used to control the pressure levels in pressure sources. FIG. 9B illustrates an example embodiment of a needle restrictor that can be used instead of valve(s) at the various ports of the pressure sources.

Example 6

In some example embodiments, a Bluetooth-capable control console (such as smartphone, computer, remote controls, etc.) can be used with the system (e.g., the system 100 and/or the system 200) to provide a user-interface for users. A user-defined software application and/or protocol can be implemented in both microcontrollers and control console (e.g., the control component 140) for operation and/or monitoring purposes. A Bluetooth module(s) can be connected with a microcontroller(s) to communicate with the control console. Operation commands (defined in software application protocol), received from control console, can be bypassed to other microcontrollers using Inter-Integrated Circuit (I2C) communication protocol.

Example 7

In some example embodiments, reagents and/or samples used in a biological assay or experiment can be stored on the system 100 and/or the system 200 in one or more pressurized container (e.g., the reagent containers 170*a-n*) with interfaces to microfluidic devices (e.g., the microfluidic component 166). An extra air pressure inlet (e.g., an extra pressure source) with a long needle that merges into stored reagent can be implemented for liquid mixing before biological assays or experiments. In-container liquid mixing can also be achieved by, for example shaking, stirring, etc. Reagents and/or samples can also be stored in the microfluidic devices/components themselves, based on technologies such as lyophilization, and/or sealed pouch (liquid form), etc.

Example 8

In some example embodiments, a handheld automated fluid handling system includes a pneumatic system capable of generating multiple pressure sources of different levels, one or more microfluidic chips with or without on-chip elastomeric valves, one or more pressure sensors and control electronics, a wireless communication module, and a control console.

The pneumatic system can contain a miniature air pump (such as a DC diaphragm pump or other types of air pumps), a number of solenoid valves (direct act type or latching type), a number of pressure reservoirs, pneumatic connections, pressure sensors, and control electronics.

The pneumatic system can use one air pump and numerous solenoid valves to generate multiple stabilized pressure sources of different levels, whose maximum values are limited by the power of the air pump. Each of the generated pressure levels is monitored by a barometric sensor, which converts air pressure level to electrical signal, in real-time. The signal is acquired by a microcontroller with ADCs. The pressure generation, stabilization and control can be controlled by multiple microcontrollers.

In some cases, the microfluidic chips can be pressure-driven microfluidic chips without on-chip valves. In some cases, the microfluidic chips can include on-chip elastomeric valves, where the valve operation relies on mechanical deformations of on-chip elastomeric membranes or structures as described in these references: U.S. Pat. Nos. 5,593,130, 4,858,883, and 8,104,515; M. A. Unger, H. P. Chou, T. Thorsen, A. Scherer A, and S. R. Quake, *Science,* 2000, 288, 113-116; K. Hosokawa and R. Maeda, *J. Micromech. Microeng.,* 2000, 10, 415; and W H Grover, A M Skelley, C N Liu, E T Lagally, and R A Mathies, *Sensors and Actuators B: Chemical,* 2003, 89 (3), 315-323. The disclosure of each of these is incorporated herein by reference in its entirety.

The microfluidic chips can be made of an elastomer material, such as polydimethylsiloxane (PDMS), or made of a combination of polymers, glass and a elastomer such as PDMS.

The microfluidic chips can include hydrodynamic trap arrays as described in H. Tan and S. Takeuchi, *Proc. Natl. Acad. Sci.,* 2007, 104, 1146-1151 (incorporated herein by reference in its entirety), for immobilizing capture-antibody coated microspheres (beads) or other particles under analysis such as cells, embryos or small organisms. The microfluidic chips can also include on board reagents for sandwich immunoassay, a sample inlet port, and on-chip valves for controlling the immunoassay liquid handling steps such as blocking, washing, incubation, mixing, and/or the like. In some cases, the fluid handling is used for an enzyme linked immunosorbent assay (ELISA), a fluorescence immunoassay, a chemiluminescence immunoassay, polymerase chain reaction (PCR), fluorescence in situ hybridization (FISH), flow cytometry, nucleic acid sequencing, air or water quality testing.

The microfluidic chips can be used to perform a bead-based sandwich fluorescence immunoassay (FIA). The microfluidic channels are first blocked by a blocking buffer to reduce nonspecific binding. Then capture antibody-coated polystyrene microbeads are loaded and immobilized by the microfluidic hydrodynamic traps (see H. Tan and S. Takeuchi, *Proc. Natl. Acad. Sci.,* 2007, 104, 1146-1151). Microbeads of different sizes can be immobilized at different locations for multiplexed detections. Then after a washing step, sample solution is loaded into the reaction chamber and allowed to incubate. During the incubation, the liquid flow is controlled to move back and forth to facilitate mixing and target binding. The sample loading and incubation step is repeated 10 times. After another washing step, fluorescently labelled detection antibodies will be loaded and allowed for incubation. Finally excess detection antibodies will be washed away and the microbeads are then ready fir fluorescence read-out.

The pneumatic system can generate multiple pressures to drive fluid flow in the microfluidic chips, and to actuate on-chip elastomeric valves on the microfluidic chips. The control console can be a wireless-capable (Bluetooth, WiFi, ZigBee, etc.) smartphone, or computer, or stand-alone control board. The control console and/or the control electronics can implement a user-defined software application protocol for fluid control, system operation, monitoring, calibration, and communication purposes. The control console can be connected to the control electronics via an wireless communication protocol such as Bluetooth, WiFi, ZigBee, and/or the like.

Example 9

Figure 10A:
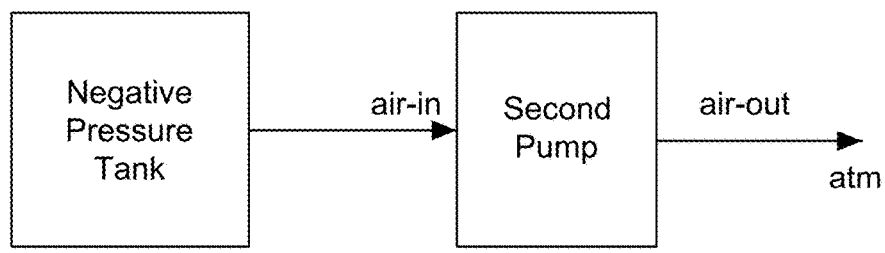
FIG. 10A is an example illustration of a negative pressure source.

FIG. 10A illustrates how negative pressure can be generated in the system 100 and/or the system 200. In this example embodiment, a second reference pressure source ("second pump") can generate negative pressure in a pressure reservoir ("negative pressure tank"), and vent the drawn air/gas to the atmosphere. The pressure reservoir/negative pressure tank can then be couple to any of the primary and/or secondary pressure sources to provide a source of negative pressure.

Figure 10B:
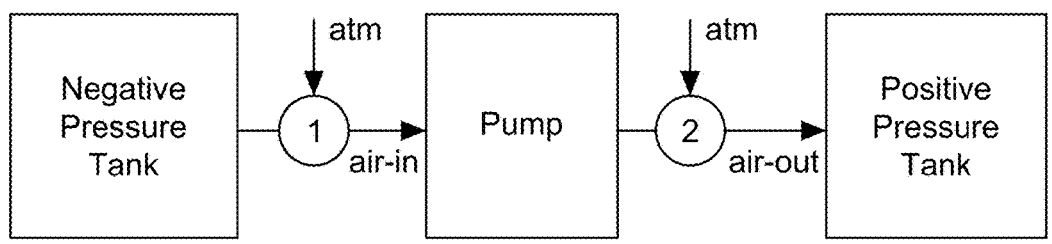
FIG. 10B is an example illustration of a pump generating a negative pressure source as well as acting as a positive pressure source.

FIG. 10B illustrates an example embodiment of how the same reference pressure source ("pump") can serve as a positive pressure source to a pressure reservoir ("positive pressure tank") and can also generate negative pressure in a pressure reservoir ("negative pressure tank"), which in turn can be connected to other pressure sources. In this example, valves "1" and "2" can be optional, 3-way solenoid valves. Depending on either the pump increasing the pressure of positive pressure tank, or decreasing the pressure of negative pressure tank, or a differential rate of doing both, the solenoid valves can be controlled to remove excess air/gas to the atmosphere.

Example 10

Figure 11A:
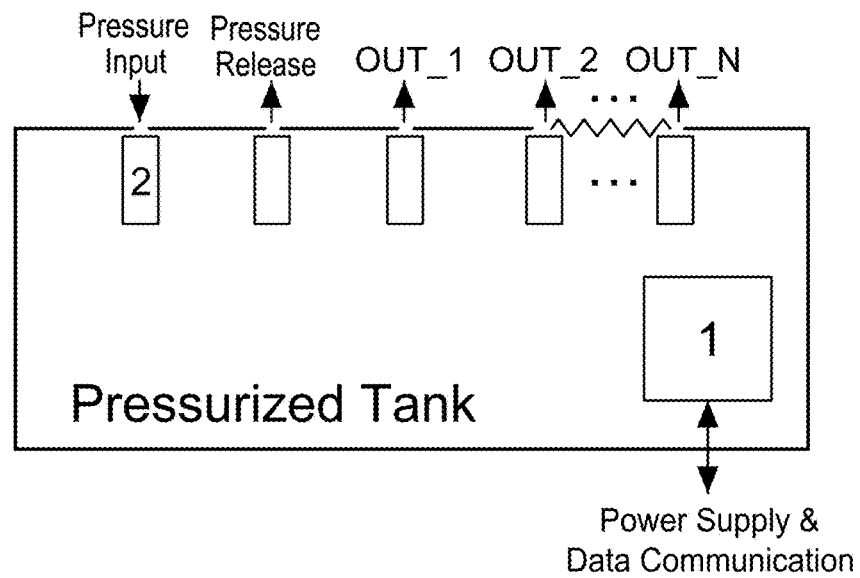
FIG. 11A is an example illustration of a pressure tank.

FIG. 11A illustrates an example embodiment of a pressure tank ("pressurized tank"). In this example, both the footprint and power consumption of the system (e.g., the system 100 and/or the system 200) can be reduced by employing the illustrated embodiment that integrates solenoid valve(s), control circuits, and other necessary components into the volume of the pressure tank. As illustrated, the pressure tank can include a pressure input port having a solenoid valve ("component 2"), a pressure release port (e.g., for releasing air/gas to the atmosphere), and multiple outlet ports OUT_1 . . . OUT$_N$. The component "1" can be electronic circuit with barometric sensors to monitor the pressure inside the pressure tank. The component "1" can also include power switching circuits to control the built-in solenoid valves (e.g., the solenoid valve illustrated as component "2" at the "pressure input" port). The component "1" can carry out data communication with external systems can be if necessary.

Figure 11B:
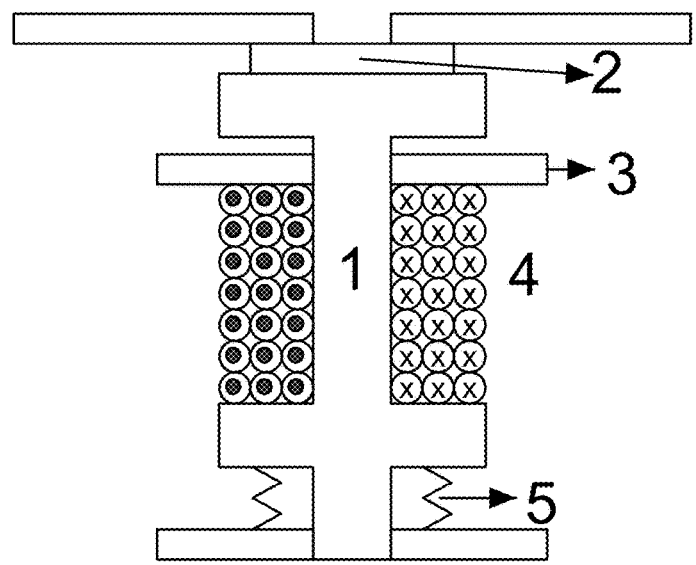
FIG. 11B is an example illustration of a solenoid valve.

FIG. 11B illustrates an example of a solenoid valve in a pressure tank (e.g., the "component 2" of FIG. 11A). The solenoid valve includes: "1"—permanent magnet plunger for moving the solenoid valve between an open and closed position; "2"—Sealing material, such as PDMS, a sealing O-ring, rubber, and/or the like; "3"—a stopper that limits the movement of plunger; "4"—coil(s) to actuate the magnetic plunger "1"; and "5"—spring(s) to close the solenoid valve when it is not actuated (i.e., maintain the solenoid valve in a "normally closed" position).

Example 11

A handheld automated microfluidic liquid handling system is presented that is controlled by a smartphone, which is enabled by combining elastomeric on-chip valves and a compact pneumatic system. The system can automatically perform all the liquid handling steps of a bead-based sandwich immunoassay on a multi-layer PDMS chip without any human intervention. The footprint of the system is 6×10.5× 16.5 cm, and the total weight is 829 g, including battery. Powered by a 12.8V 1500 mAh Li battery, the system consumed 2.2 W on average during the immunoassay and lasted for 8.7 hrs. This handheld microfluidic liquid handling platform is generally applicable to many biochemical and cell-based assays requiring complex liquid manipulation and sample preparation steps such as FISH, PCR, flow cytometry and nucleic acid sequencing. In particular, the integration of this technology with read-out biosensors may help enable the realization of the long-sought Tricorder-like handheld in-vitro diagnostic (IVD) systems.

A smartphone-controlled handheld microfluidic liquid handling system is provided by combining elastomeric on-chip valves and a handheld pneumatic system. The handheld pneumatic system provides on-board multiple pressure generation and control by using a miniature DC diaphragm pump, pressure-storage reservoirs, and small solenoid valves. This system is applicable to both single-layer pressure-driven microfluidics and multi-layer elastomeric microfluidics. Elastomeric microfluidics include microfluidic systems with on-chip valves based on the mechanical deformations of elastomeric membranes or structures, such as multi-layer PDMS microfluidics, glass/PDMS/glass devices, or other hybrid devices.

In a typical elastomeric microfluidic system, at least two different pressure sources are needed: one for actuating on-chip valves, which typically require a pressure level higher than 10 psi; and the other for driving reagents into microfluidic channels (for typical microfluidic channel dimensions, e.g. 10 μm high, 100 μm wide, 1 to 5 psi is sufficient). Traditionally, this is achieved by using two pressure regulators connected to a compressed gas tank. However, the sizes and nature of these components make them unsuitable for building a handheld system. Although it is possible to use two miniaturized diaphragm pumps to build such a system, the significant fluctuations of the output pressure of a diaphragm pump limit its applications.

Figure 12:
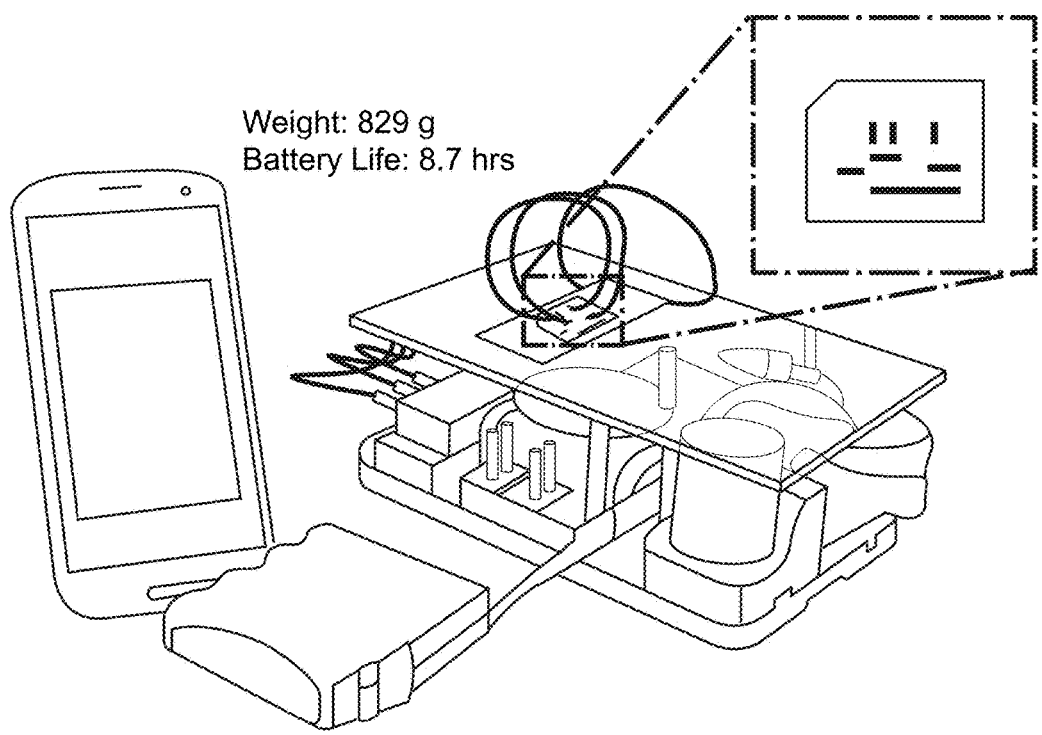
FIG. 12 is an image of a example smartphone-controlled handheld microfluidic liquid handling system. The footprint of the instrument is 6×10.5×16.5 cm. Powered by a 12.8V 1500 mAh Li battery, the instrument consumes 2.2 W on average for a typical sandwich immunoassay and lasts for 8.7 hours. Inset is a magnified view of a multi-layer PDMS device with on-chip elastomeric valves.

To address these challenges, presented here is a handheld microfluidic liquid handling system controlled by a smartphone (FIG. 12), which can provide two different pressure sources and an array of 8 pneumatic control lines for operating elastomeric microfluidic chips. One pressure source is set to above 10 psi (max. 20 psi) to operate on-chip elastomeric valves; while the other can be set to any value below 5 psi to drive liquid flow, with a precision of ±0.05 psi. Eight independent pneumatic control lines are available to handle eight different reagents. The footprint of the resulting system is 6×10.5×16.5 cm, and the total weight is 829 g (including battery). The system can operate continuously for 8.7 hours while running an immunoassay liquid handling protocol when powered by a 12.8 V, 1500 mAh Li battery. This technology can serve as a general purpose small volume liquid handling platform for many biochemical and cell-based assays such as fluorescence in-situ hybridization (FISH), PCR, flow cytometry and nucleic acid sequencing. The integration of this system with biosensors may help realize the long-sought dream of handheld multi-analyte in-vitro diagnostic (IVD) systems, i.e. Medical Tricorders.

The overall handheld system consists of three subsystems: (1) a pneumatic pressure generation and control subsystem (Pneumatic subsystem); (2) an electronic printed circuit board (PCB) with 2 microcontrollers, a Bluetooth communication module, pressure sensors and power device drivers (Electronic subsystem); and (3) an elastomeric microfluidic chip (Microfluidic chip). The system can be controlled by a Bluetooth enabled Android smartphone (Galaxy S III).

Pneumatic Subsystem

The pneumatic subsystem is designed to generate two compressed air pressure sources at different levels (P1: >10 psi; P2: 0 to 5 psi) for operating elastomeric microfluidics. Two pressure reservoirs, labelled as Reservoir 1 and Reservoir 2. (FIG. 13), are used to store compressed air. A miniature DC diaphragm pump is used to pump air into Reservoir 1 to generate the primary pressure source for actuating on-chip elastomeric valves. A secondary pressure source, stored in Reservoir 2, is derived from Reservoir 1 and stabilized by a feedback control system with a precision of ±0.05 psi for driving liquid reagents through microfluidic channels. The system can be easily extended to have multiple secondary pressure sources of different pressures if required.

Figure 14:
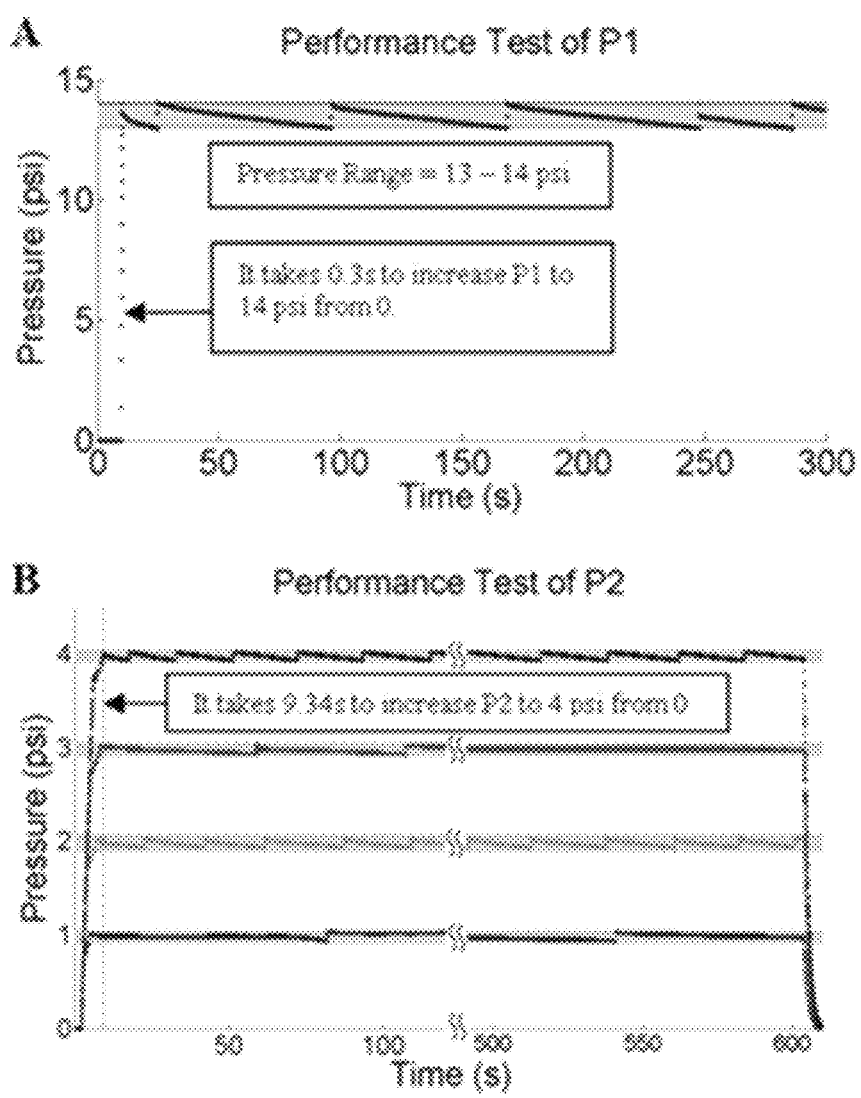
FIGS. 14A-14B illustrate the results of pneumatic performance tests on the system of FIGS. 13-13.

Each pressure reservoir is made of four segments of ⅛" ID Tygon tubing connected with a four-way barbed cross connector, leaving four open ports. Each open port of a reservoir is connected to a functional part of the pneumatic subsystem (such as a diaphragm pump, a solenoid valve or a pressure sensor, as shown in FIG. 14 and described in more detail below) via a barbed connector. The volume of each reservoir is determined by the total length of tubing used. Here, the volumes of Reservoir 1 and 2 are 6.2 mL and 16.2 mL, respectively.

The four open ports of Reservoir 1 are connected to the following components, respectively:

(1) A miniature DC diaphragm pump (Parker, H004C-11), used to generate the primary pressure source for the system. A check valve in-between is used to prevent air leakage when the pump is off.

(2) Barometric Sensor 1, to monitor the pressure level in Reservoir 1.

(3) The normally open (N.O.) port of a solenoid valve manifold with eight channels (Pneumadyne, MSV10-8), each common port of this manifold is connected to an on-chip elastomeric valve.

(4) The common port of a solenoid valve (Valve 1, Pneumadyne, S10MM-30-12-3) with base (Pneumadyne, MSV10-1), to generate the secondary pressure source (P2, between 0 and P1 typically 0-5 psi). A plastic needle valve restrictor (Poweraire, F-2822-41-B85-K) is placed before the common port of Valve 1 to limit the air flow into Reservoir 2.

The four open ports of Reservoir 2 are connected to the components given below, respectively:

(1) The normally closed (N.C.) port of Valve 1 described above. Once the pressure in Reservoir 2 drops to below the lower bound of the target pressure range, Valve 1 will be opened to increase the Reservoir 2 pressure gradually. Another plastic needle valve restrictor (Poweraire, F-2822-41-B85-K) is used to fine tune the flow rate of air to reduce excessive pressure overshoot in Reservoir 2. The N.O. port of Valve 1 is completely sealed with PDMS to mimic a 2-way N.C. valve.

(2) The N.C. port of a solenoid valve (Valve 2) to release pressure in Reservoir 2. The common port of Valve 2 is sealed with PDMS, resulting in a small internal air volume (~250 µL). By toggling the state of Valve 2, its internal volume is connected to either Reservoir 2 or atmosphere. When Reservoir 2 is connected to Valve 2's internal volume, the pressure in Reservoir 2 drops by a small amount due to volume expansion. Immediately following this, the pressure in Valve 2's internal volume is released by connecting it to atmosphere. By choosing the appropriate Reservoir 2 volume, the pressure release can be controlled precisely to achieve the desired pressure resolution.

(3) Barometric Sensor 2, to monitor the pressure level in Reservoir 2.

(4) The N.C. port of a solenoid valve (Valve 3), to drive reagents into a microfluidic chip. The common port of Valve 3 is divided into multiple lines, each connected to a reagent container (a modified micro-centrifuge tube). Once it is actuated, the pressure stored in Reservoir 2 is applied to every reagent container in the system.

Microcontroller-Based Electronic Subsystem

Two ATMega328p 8-bit microcontrollers were used in the PCB design. The first microcontroller is responsible for four tasks: (1) receive commands from a smartphone via Bluetooth 2.1 (Bluetooth Mate Silver, Sparkfun, WRL-12576), (2) pass commands to the second microcontroller, (3) request real-time barometric sensor data from the second microcontroller and send it to the smartphone at a frequency of 50 Hz, and (4) control the status of 6 load switch circuits for pump and solenoid valve operation. The second microcontroller also has four functions: (1) control the status of the other 12 load switch circuits (making the system capable of operating 18 electromechanical components (valves or pumps)), (2) monitor the barometric sensor data with the built-in 10-bit ADCs, (3) automatically adjust pressure levels in the two pressure reservoirs, and (4) send barometric sensor data to the first microcontroller on request. Communication between these two microcontrollers is realized with the Wire Library provided by Arduino, which enables bi-directional communication via only two wires using the $I^2C$ protocol.

Two barometric sensors (Measurement Specialties, 1240-015D-3L) are used to acquire real-time pressure data in the pneumatic subsystem. Electrical sensor output data are amplified by two instrumentation amplifiers (Texas Instruments, INA114). Two general-purpose rail-to-rail operation amplifiers (Texas Instruments, OPA2171) were used to shift the signal level to between 0 and 5 V before connecting to the 10-bit ADCs of the second microcontroller. Each barometric sensor is calibrated with a commercial grade sanitary pressure gauge (Ashcroft, 1035). The calibration curve is saved in the microcontrollers Flash memory.

The PCB circuit is powered by a 12.8 V $LiFePO_4$ battery pack with a capacity of 1500 mAh. This battery is directly used as the power supply to an array of 18 load switch circuits to power solenoid valves and the diaphragm pump. Each output of the load switch circuit is wired to a screw terminal block (Sparkfun, PRT-08084), into which the power wires of the valves and pump are mounted. The battery is also regulated by a 5V regulator to power the PCB (microcontrollers, Bluetooth module, Barometric Sensors & OpAmps). FIG. 21 illustrates an example PCB circuit design.

Pressure Stabilization in Reservoir 1 and 2

The pressure levels in the two reservoirs of the pneumatic subsystem are automatically adjusted by a feedback control algorithm programmed in the second microcontroller, with the barometric sensor as the feedback sensor, and the diaphragm pump and solenoid valves (Valve 1 & 2) for pressure control. A user only needs to set the upper and lower bounds of both pressure levels through the smartphone interface.

Reservoir 1, which contains higher pressure (>10 psi) to actuate on-chip valves and serves as the pressure source for Reservoir 2, is directly pressurized by the diaphragm pump. If the pressure level drops to below the chosen lower bound detected by Barometric sensor 1, the pump starts to run until the pressure is restored to the target upper bound.

The pressure in Reservoir 2 is used to drive liquid reagents through microfluidic channels, and the required pressure level is relatively low (normally below 5 psi for typical microfluidic channel dimensions of 10-100 µm). However, it is desirable to be able to precisely change the Reservoir 2 pressure in seconds. In order to obtain a stable Reservoir 2 pressure, instead of directly using the diaphragm pump as the pressure source, Reservoir 1 was used as a buffered pressure supply, connected to Reservoir 2 via a 2-way N.C. solenoid valve (Valve 1). As described above, another 3-way solenoid valve (Valve 2) is used to precisely release pressure in a stepwise fashion. If a pressure below the set lower bound is sensed, Valve 1 will be opened. Conversely, if the pressure exceeds the higher bound, Valve 2 starts to operate to decrease the pressure in Reservoir 2.

Microfluidic Device Fabrication, Reagent Containers, and Interfaces

A PDMS elastomeric microfluidic chip was fabricated using multi-layer soft lithography for bead-based sandwich florescence immunoassays. The on-chip valves were operated in a push-down configuration (flow layer on the bottom). The master molds were fabricated using standard UV photolithography with AZ50XT positive photoresist. The control layer was made by pouring a PDMS mixture (RTV615 A:B at a 5:1 ratio) onto the mold and baking it for 1 hour at 65° C. For the flow layer, a PDMS mixture at a 20:1 ratio was spin-coated onto the flow layer mold at 3000 rpm for 1 minutes and baked at 65° C. for 30 minutes. After curing of these two layers, the control layer was peeled off from the mold, aligned and placed it on top of the flow layer, followed by a 2 hour bake. Then the device was peeled off the flow layer mold and bonded to a glass slide by air plasma treatment.

The reagent containers were modified 1.5 mL disposable microcentrifuge tubes (Ted Pella MC-6600, polypropylene). The lid of every tube was punched by a 21 gauge needle to form two holes. Two 21 gauge needles of different lengths were inserted into the holes. The longer needle was immersed in the liquid reagent, while the shorter one was above the liquid surface for pressurization. By storing the reagents in the tubes, and applying air pressure through the shorter needle, the reagents were pushed out from the longer needle. Interfaces between the pneumatic subsystem, the reagent containers, and the microfluidic devices were made of Tygon tubing and 21 gauge needles.

Simulated Bead-Based Fluorescence Immunoassay Liquid Handling

The system was used to perform all the liquid handling steps of a bead-based sandwich fluorescence immunoassay (FIA). Three coloured food dyes were used to simulate the reagents used in the immunoassay. The detailed 10-step FIA protocol (liquid handling sequences) is shown in Table 3 below. The microfluidic channels are first blocked by a blocking buffer to reduce nonspecific binding. Then capture antibody-coated polystyrene microbeads are loaded and immobilized by the microfluidic hydrodynamic traps. Microbeads of different sizes can be immobilized at different locations for multiplexed detections. Then after a washing step, sample solution is loaded into the reaction chamber and allowed to incubate. During the incubation, the liquid flow is controlled to move back and forth to facilitate mixing and target binding. The sample loading and incubation step is repeated 10 times. After another washing step, fluorescently labelled detection antibodies will be loaded and allowed for incubation. Finally excess detection antibodies will be washed away and the microbeads are then ready for fluorescence read-out.

TABLE 3

Simulated Immunoassay Liquid Handling Protocol

| | |
|---|---|
| 1. | Fill the device with blocking buffer (Green, 5 s). |
| 2. | Incubate (5 min). |
| 3. | Load washing buffer (Clear, 5 min). |
| 4. | Load beads (Red, 10 s) |
| 5. | Load washing buffer (Clear, 5 min). |
| 6. | Load sample (Red, 5 s) and incubate (1 min). Repeat step 6 ten times. |
| 7. | Load washing buffer (Clear, 5 min). |
| 8. | Load detection antibody (Green, 5 s) and incubate (1 min). Repeat step 8 ten times. |
| 9. | Load washing buffer (Clear, 5 min). |
| 10. | Ready for detection |

Android Smartphone Application

An Android (version 4.2) app with a graphical user interface (GUI) was written to allow user control of the system, and the display and analysis of collected data. An application protocol was designed and implemented it in both the smartphone app and ATMega328 microcontrollers. This application protocol has three basic functions: (1) set the status of each solenoid valve, (2) set the target pressure range of each reservoir, and (3) request barometric sensor readings from the microcontroller. The protocol of the simulated immunoassay is programmed in this Android application, using these three fundamental functions, to achieve liquid manipulation and monitor the pressure levels of the reservoirs.

Results and Discussion

The pneumatic performance of the system was characterized, including achievable pressure range, pressure stability, response time, and leakage rate. Reservoir 1 was tested under no loading conditions, with a target pressure range of 13-14 psi. The maximum achievable pressure was about 20 psi limited by the diaphragm pump. Starting from 0 psi, it took about 0.3 second to rise to 14 psi (FIG. 14A). The pressure dropped by about 1 psi every minute, and the pump automatically started to restore the pressure in Reservoir 1. This level of pressure leakage, although preventable by better sealing, does not affect the actuation of on-chip valves, nor the pressure level in Reservoir 2 due to the feedback pressure stabilization mechanism described above.

Reservoir 2 was tested and characterized with a simple one-channel pressure driven microfluidic chip as the load. Coloured food dye was pushed into the microfluidic channel (500×20 μm, W×H) continuously. Four integer pressure levels below 4 psi (1, 2, 3, 4 psi) were tested, with a tolerance of ±0.05 psi. The measured results are shown in FIG. 3B. It took about 10 seconds for the pressure in Reservoir 2 to rise to 4 psi, which is much longer compared with that of Reservoir 1. This is because two needle valve restrictors were used to limit the flow rate between Reservoir 1 and Reservoir 2 to improve stability. During the 10-minute test, the pressure was completely controlled in the target pressure ranges. At the end of the tests, the target pressure was set to 0 psi to examine the performance of pressure release. The results were comparable to theoretical calculations from ideal gas law.

During the tests, it was found that the volume of a reservoir, especially Reservoir 2, had a significant influence on the performance. Whenever the system opens a valve, the effective volume of a reservoir will increase, which leads to a pressure drop inside the reservoir. When reagents are driven into a microfluidic device, the effective volume of Reservoir 2 is also increased (FIG. 14B). Increasing the volume of a reservoir will make it less sensitive to volume changes. However, this will increase the size of the system, which is undesirable for a handheld system. Moreover, increasing the volume of Reservoir 2 makes it respond slower when changing the target pressure settings. It was found that the parameters listed above gave sufficient performance for immunoassay applications, but there is still room for improvements by optimizing the air flow rate and volumes of reservoirs.

Improving the sealing of the pneumatic system will also improve the overall performance of the system, in terms of pressure and power. No special effort was made to ensure that the system was completely airtight, as the pressure performance was sufficient for our applications. However, it is desirable and feasible to improve the sealing in the future with better pneumatic connections and components, so that the system can be more stable and consume less power.

Figure 16:
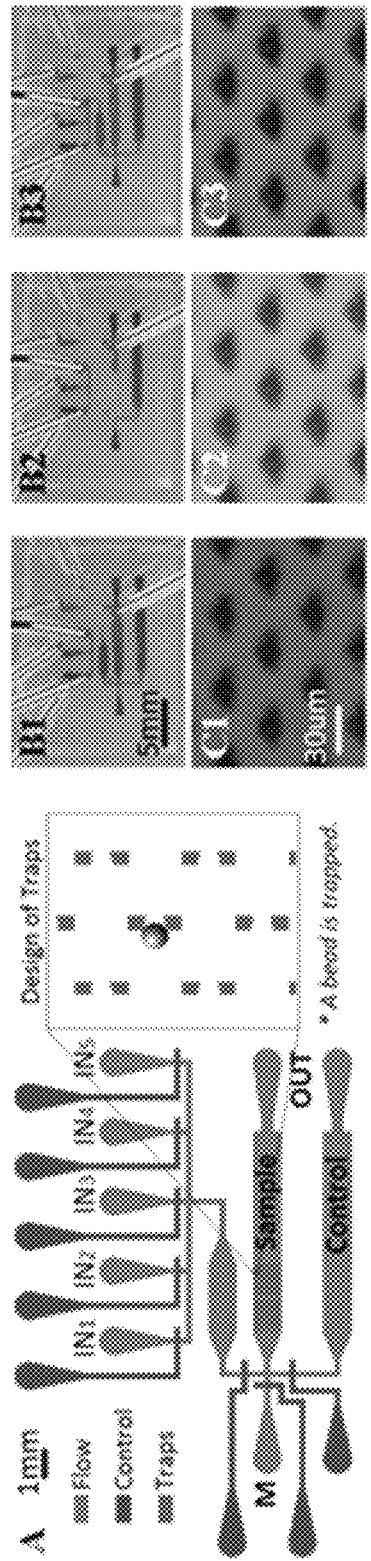

Next, the operation of on-chip valves was tested under a bright field optical microscope. It was validated that the on-chip valves could be fully closed without leakage by driving coloured food dye into the flow layer at P2=2 psi, and toggling the state of the controlling solenoid valve multiple times. The on-chip valve was completely closed when P1 was set to 13-14 psi (FIG. 16). Other PDMS devices were also with different valve geometries and configurations (both push-up and push-down), and it was found that it is possible to operate properly designed push-up valves with even lower actuation pressure down to 5 psi as reported previously.

A simulated immunoassay liquid handling protocol on a PDMS device automated by the handheld instrument and controlled by a Galaxy SIII smartphone was demonstrated. The design layout of the PDMS device is shown in FIG. 16A. The device has five inlet ports, two reaction chambers (sample and control), and one outlet port. Each inlet port is supplied with one of the following reagents: blocking buffer (e.g. PBS+0.1% Tween-20+0.5% BSA), washing buffer (e.g. PBS+0.1% Tween-20), capture antibody-coated polystyrene microbeads, sample, and fluorescently labelled detection antibodies. Inside the reaction chambers, arrays of hydrodynamic traps with openings of different sizes are used to immobilize individual capture antibody coated microbeads at predefined locations. Sequential traps of different sizes (larger sizes upstream) can be used to trap different sized microbeads for multiplexed detection. Once the microbeads are immobilized, subsequent mixing, washing and incubation steps can be easily performed on them under well controlled flow conditions.

Figure 15:
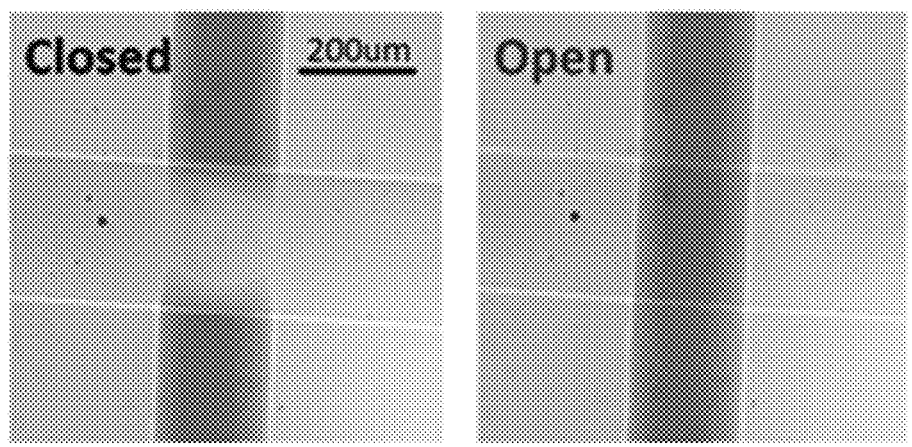
FIG. 15 illustrates an example demonstration of operation of an on-chip elastomeric valve under an optical microscope. Colored food dye was flowed through the microfluidic channel and the state of the on-chip valve was toggled. P1 was set to 13-14 psi, and P2 was set to 2 psi.

During the incubation steps, the liquid flow can be controlled to move back and forth by pressurizing port M (FIG. 16A) and the output port alternatively to facilitate mixing and target binding. For every test, all reagents except for the sample solution are loaded into both reaction chambers, following the sequence of a typical sandwich florescence immunoassay protocol. Sample solution will be loaded only into the sample chamber, leaving the other chamber as a control. All wastes is discharged from the outlet port, and collected by a disposable microcentrifuge tube. A 10-step simulated fluorescence immunoassay protocol (Table 1) was designed, which took about 50 minutes to complete. This protocol was programmed in the Android application, and could be easily modified by the user. Two different coloured food dyes and water were used to simulate various reagents. Screenshots of various liquids flowing inside the microfluidic device are shown in FIG. 15.

Figure 17:
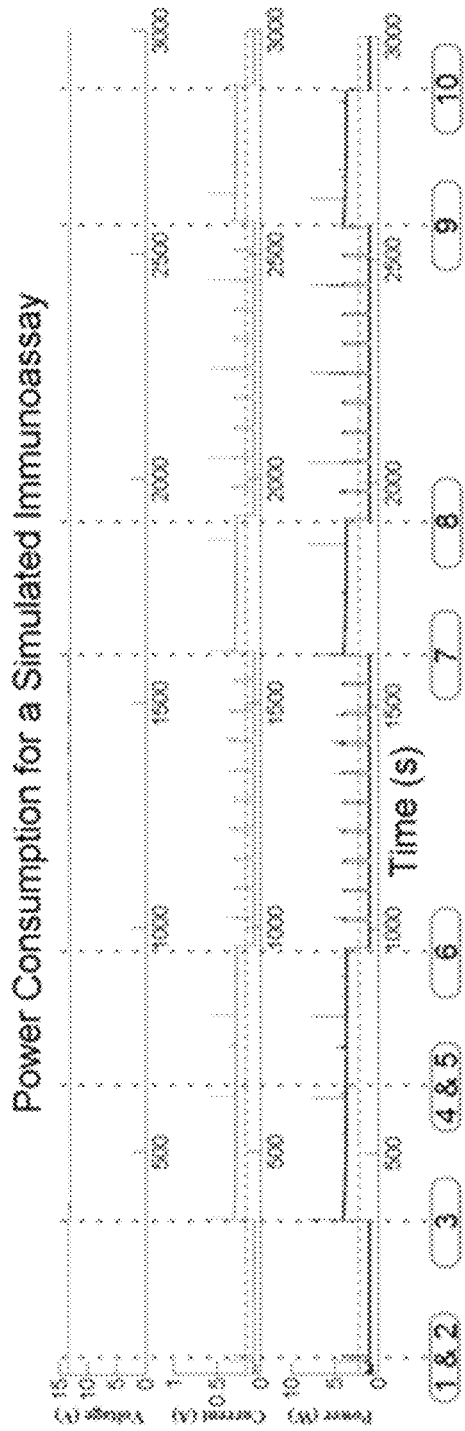
FIG. 17 illustrates, according to an example, power consumption for running the simulated immunoassay protocol of Table 1. A digital multimeter (DMM) was connected to the system to measure the voltage (V) and current (I) of the batter at a frequency of 10 Hz. Power consumption was then calculated as P=V1. The immunoassay protocol took about 50 minutes to complete. Horizontal dashed lines (black) indicate the average values of the measured parameters.

Power consumption can be a critical performance metric of a handheld system. A digital multimeter (Keithley, Model 2000) was used to record the voltage and current changes at a sampling rate of 10 Hz while running the simulated immunoassay protocol. Power consumption was obtained by multiplying the voltage with the current (FIG. 17). The average power consumption during the simulated immunoassay was 2.2 W. As the capacity of the battery used was 19.2 Whr, the system could last for 8.7 hours on one full charge.

The average power consumption of 2.2 W can be further reduced by 0.65 W by replacing the normally closed (N.C.) solenoid valve (Valve 3) at the output of Reservoir 2 with a normally open (N.O.) one. Additionally, if the solenoid valves are replaced with latching solenoid valves or use a 'Spike and Hold' circuit, the power consumption can be further reduced to less than 1 W. It was also found that when the system was idle (no solenoid valves are operating), it still consumed 0.98 W of power, which can be reduced by redesigning the circuit with low power microcontrollers and electronic components. The system operation time can also be extended by using a higher capacity battery. For example, four 2600 mAh cell phone Li batteries (3.7V) can theoretically power the device for 25 hours on a full charge, thus permitting full day operation.

The current system footprint is 6×10.5×16.5 cm (H×W×L), and the total weight is 829 g (including battery). By improving the design and choosing more compact components, it is feasible to reduce the weight to below 1 pound (454 g), and reduce the size by a half in the future. With better designed microfluidic devices, once can also decrease the pressure required for actuating on-chip valves, and consequently, further reduce the power consumption, size and weight of the whole system.

Demonstrated herein is a smartphone-operated fully automated handheld pneumatic liquid handling system for elastomeric microfluidics. In addition to traditional multi-layer PDMS microfluidics, this system is also applicable to other types of elastomeric microfluidics such as devices similar to GE's Biacore™ SPR chips, glass/PDMS/glass devices and other hybrid devices. This general purpose handheld liquid handling system is an enabling technology, which can find broad applications in point-of-care medical diagnostics, environmental testing, food safety inspection, biohazard detection, and biological research. In particular, the integration of this technology with read-out biosensors may one day help enable the realization of the long-sought Tricorder-like handheld IVD systems.

Example 12

Barometric Sensors Calibration

Two barometric sensors (e.g., the sensors 150, 160) are used to monitor the pressure levels in Reservoir 1 (e.g., the primary pressure source 120) and 2 (e.g., the secondary pressure source 130). In the example designs disclosed herein, the resolution of digitized pressure reading is 0.02 psi (ADC reading of 1), while the maximum pressure of the system is 14 psi (ADC reading of 700). To calibrate the barometric sensors, a regulated pressure source (generated by a gas tank, a pressure regulator, and a dial pressure gauge; see FIG. 18A for setup) is used following the steps given below:

(1) Open the gas tank, and tune the pressure regulator to supply both barometric sensors with 14 psi air pressure.

(2) Adjust both gain resistors of the instrumentation amplifiers to make both ADC readings to 700.

(3) After 20 s of recording, decrease the pressure supply by 1 psi by adjusting the pressure regulator.

(4) Repeat step 3 until the pressure supply reaches 0 (excluding 1 psi, limited by the dial pressure gauge).

(5) Export the recorded data to a computer, and process with MATLAB—(a) take 10 s of recording from each segment of data of different pressure levels (FIG. 18B); (b) plot the average value of each segment of extracted data vs. the pressure levels (FIGS. 18C, 18D); (c) find the calibration curve by fitting the data points with a straight line (FIGS. 18C, 18D).

Here, the fitted calibration curves are:

$$\begin{cases} ADC_1 = 51.347 \cdot P_1 - 24.443 \\ ADC_2 = 51.133 \cdot P_2 - 20.833 \end{cases}$$

These two functions can be programmed into the microcontrollers to identify the calibrated ADC values according to the given pressure values.

Example 13

Fabrication of Liquid Reagent Containers

A miniaturized container, modified from a microcentrifuge tube, was used to hold the liquid samples and reagents. In this example, dfabrication details are as described below:

(1) Prepare one microcentrifuge tube with lid, and two 21 gauge needles (FIG. 19A).

(2) Penetrate through the lid with two needles, one longer (reaching the bottom of the tube) and the other shorter (above the liquid) (FIG. 19B).

Seal the lid with PDMS to prevent air leakage (FIG. 19C).

Fill liquid reagent or sample into the tube, and connect the tube to the system with Tygon tubing (FIG. 19D).

Example 14

Design of Software Architecture

The Android application developed has two tabs: one for running a simulated immunoassay protocol; and, the other for testing and calibrating each individual function of the system. In this example, it has the following functions (FIGS. 20A-20C):

(1) When a user starts to run the Android application after the system is powered up, the program automatically searches for target Bluetooth device and establishes connection. After the connection is set up, the program will command the system to increase the target pressure of Reservoir 1 (e.g., the primary pressure source 120), for on-chip valve actuation, to a range of 10 to 14 psi; and set the pressure of Reservoir 2 (e.g., the secondary pressure source 130), for liquid driving, to 0 psi. The user can adjust the progress bar at the bottom to change the target pressure of Reservoir 2. Real-time data from the barometric sensors is collected from the system at a sampling rate of 50 Hz, and plotted using Android plot 0.6.0 library (FIG. 20A). One can press the start button to run the simulated immunoassay protocol. During experiments, the abort or exit button could be used to terminate the immunoassay process.

(2) Once the protocol button is pressed, the immunoassay protocol will be displayed (FIG. 20B). This protocol is programmed in the smartphone application, and explained in a message box. A user can modify the program to adapt to different applications.

When the TEST tab is selected, the window for testing individual function shows up (FIG. 20C). It is grouped into three sections. Buttons in the first section are for controlling the ON/OFF status of the output valves. The second section is for setting the target pressures of the two reservoirs. The last section displays the readings and calculated pressure values (in PSI). The record button at the bottom is to save collected data to a text file, which could be used for calibration and other purposes.

Communication between the android app and microcontrollers are realized by a customized software application protocol, which uses one ASCII character to represent a specific instruction. This application protocol has three fundamental functions: (1) change the state of an output port (solenoid valve or pump), (2) set target pressure ranges of P1 and P2, and (3) acquire real-time barometric sensor data from the microcontrollers. Detailed design is listed in Table 4.

TABLE 4

| Command | Explanation | Command | Explanation |
|---|---|---|---|
| Uppercase A to R | Activate load switch circuit 1-18 | Lowercase a to r | Deactivate load switch circuit 1-18 |
| Y/y | Enable/disable acquiring barometric sensor data from the microcontrollers | Z/z | Reset the system |
| !__ | Set the target pressure range of Barometric Sensor 1 | @__ | Set the target pressure range of Barometric Sensor 2 |

These two commands, '!' and '@', should be followed by a sequence of four character. Every two chars are representing the lower and upper part of a short value, respectively. Four characters will be converted into two short values in the microcontrollers, which specify the lower bound and upper bound of the target pressure level (ADC readings).
For example:
  [Android App]
  send !AABB
  [Microcontrollers on receive !AABB]
  Lower Bound of Barometric Sensor 1 = 16705//AA
  Upper Bound of Barometric Sensor 1 = 16962//BB Example 15

FIG. 21 illustrates an example PCB design, as generally discussed at least in Example 12.

In some embodiments, aspects of the disclosure are directed to a handheld automated fluid handling system (e.g., the system 100 and/or the system 200) that includes a pneumatic component/system capable of generating multiple pressure sources of different levels. Such a pneumatic component/system could include (using FIG. 1 as an example), but are not limited to, the pressure sources 110, 120, 130, the valves 116, 126, 136, 146, 156, and/or the like. The handheld automated fluid handling system can also include one or more microfluidic chips such as, for example, the microfluidic component 166. In some embodiments, at least one microfluidic chip can include on-chip elastomeric valves. The handheld automated fluid handling system can also include one or more pressure sensors, such as, for example, the sensors 150, 160. The handheld automated fluid handling system can also include control components such as, for example, the control component 140. In some embodiments, the control component can include, but is not limited to, control electronics, a wireless communication module (e.g., Bluetooth, WiFi, and/or the like), and a control console for user interaction.

In some embodiments, each of the system 100 and the system 200 includes at least a processor (not shown) and a memory (not shown). The memory in each system can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory can store instructions to cause the processor to execute modules, processes and/or functions associated with the system.

The processor can be, for example, a general purpose processor, a Field Programmable Gate Array (FPGA), an Application Specific Integrated Circuit (ASIC), a Digital Signal Processor (DSP), and/or the like. The processor can be configured to run and/or execute application processes and/or other modules, processes and/or functions associated with the system.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, .NET, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:
1. A handheld system, comprising:
   a reference pressure source configured to generate a reference pressure;
   a primary pressure source coupled to the reference pressure source, the primary pressure source configured to generate a primary pressure in a primary pressure range, the primary pressure less than the reference pressure, the primary pressure induced by the reference pressure source;
   a secondary pressure source coupled to the primary pressure source, the secondary pressure source configured to generate a secondary pressure in a secondary pressure range, the secondary pressure less than the primary pressure, the secondary pressure induced by the primary pressure source;
   a first valve configured to couple the primary pressure source to the secondary pressure source, the first valve configured to remain closed when the secondary pressure is above a lower bound of the secondary pressure range, the first valve further configured to open when the secondary pressure falls below the lower bound of the secondary pressure range; and
   a second valve coupled to the secondary pressure source, the second valve configured to regulate the secondary pressure, the second valve configured to remain closed when the secondary pressure is below an upper bound of the secondary pressure range, the second valve further configured to open when the secondary pressure exceeds the upper bound of the secondary pressure range.

2. The handheld system of claim 1, wherein the reference pressure source is a pressure pump, the primary pressure source is a primary reservoir coupled to the pressure pump, and the secondary pressure source is a secondary reservoir coupled to the primary reservoir.

3. The handheld system of claim 1, wherein the primary pressure source is a primary reservoir having a primary reservoir volume and the secondary pressure source is a secondary reservoir having a secondary reservoir volume, the secondary reservoir volume greater than the primary reservoir volume.

4. The handheld system of claim 1, wherein the reference pressure source includes one or more of the following: a DC diaphragm pump, DC brushless pump, a valve, and a gas source.

5. The handheld system of claim 1, wherein at least one of the first valve and the second valve includes a flow restrictor.

6. The handheld system of claim 1, wherein the second valve includes a normally closed two-way solenoid valve.

7. The handheld system of claim 6, wherein at least one of the first valve and the second valve includes a flow restrictor.

8. The handheld system of claim 1, wherein:
   the reference pressure source is configured to maintain the primary pressure within the primary pressure range.

9. The handheld system of claim 1, further comprising:
   a primary pressure sensor coupled to the primary pressure source, the primary pressure sensor configured to sense pressure in the primary pressure source; and
   a secondary pressure sensor coupled to the secondary pressure source, the second pressure sensor configured to sense pressure in the secondary pressure source,
   the reference pressure source configured to maintain the primary pressure within the primary pressure range based on feedback from the primary pressure sensor, and
   the second valve and the first valve configured to maintain the secondary pressure within the secondary pressure range based on feedback from the secondary pressure sensor.

10. The handheld system of claim 1, further comprising:
a control component coupled to, and configured for control of, the reference pressure source, the first valve, and the second valve,
the control component further configured to maintain the primary pressure in the primary pressure range and to maintain the secondary pressure in the secondary pressure range.

11. The handheld system of claim 1, further comprising a control component configured to maintain pressure in the primary pressure source in the first pressure range and to maintain pressure in the secondary pressure source in the second pressure range, the control component including a wireless controller.

12. The handheld system of claim 1, further comprising a microfluidic component coupled to the primary pressure source and to the secondary pressure source, the microfluidic component fabricated at least in part from an elastomeric material.

13. The handheld system of claim 1, further comprising a microfluidic component coupled to the primary pressure source and to the secondary pressure source, the microfluidic component selected from an enzyme linked immunosorbent assay (ELISA) device, a fluorescence immunoassay device, a polymerase chain reaction (PCR) device, a fluorescence in situ hybridization (FISH) device, a flow cytometry device, a nucleic acid sequencing device, and a quality testing device.

14. The handheld system of claim 1, further comprising:
a microfluidic component coupled to the primary pressure source and the secondary pressure source; and
a control component configured to maintain pressure in the primary pressure source in the primary pressure range for controlling operation of the microfluidic component, and to maintain the pressure in the secondary pressure source in the second pressure range for controlling reagent input to the microfluidic component.

15. The handheld system of claim 1, wherein the primary pressure range is from about 0 psi to about the reference pressure.

16. The handheld system of claim 1, wherein the secondary pressure range is from about 0 psi to about the primary pressure.

17. The handheld system of claim 1, further comprising a reference valve configured to couple the reference pressure source to the primary pressure source, the reference valve including a solenoid valve.

18. A handheld system, comprising:
a reference pressure source configured to generate a reference pressure;
a primary pressure source coupled to the reference pressure source, the primary pressure source configured to generate a primary pressure in a primary pressure range, the primary pressure less than the reference pressure, the primary pressure induced by the reference pressure source;
a secondary pressure source coupled to the primary pressure source, the secondary pressure source configured to generate a secondary pressure in a secondary pressure range, the secondary pressure less than the primary pressure, the secondary pressure induced by the primary pressure source;
a first valve configured to couple the primary pressure source to the secondary pressure source;
a second valve coupled to the secondary pressure source, the second valve configured to regulate the secondary pressure;
a third valve configured to couple the primary pressure source to a primary pressure outlet;
a primary pressure sensor coupled to the primary pressure source, the first pressure sensor configured to sense pressure in the primary pressure source;
a fourth valve configured to couple the secondary pressure source to a secondary pressure outlet; and
a secondary pressure sensor coupled to the secondary pressure source, the second pressure sensor configured to sense pressure in the secondary pressure source,
the primary pressure source including a primary reservoir having a primary reservoir volume defined by the reference pressure source, the primary pressure sensor, the first valve, and the third valve,
the secondary pressure source including a secondary reservoir having a secondary reservoir volume defined by the first valve, the secondary pressure sensor, the second valve, and the fourth valve.

19. The handheld system of claim 18, wherein at least one of the first valve, the second valve, the third valve, and the fourth valve includes a flow restrictor.

20. A handheld system, comprising:
a reference pressure source configured to generate a reference pressure;
a primary pressure source coupled to the reference pressure source, the primary pressure source configured to generate a primary pressure in a primary pressure range, the primary pressure less than the reference pressure, the primary pressure induced by the reference pressure source;
a secondary pressure source coupled to the primary pressure source, the secondary pressure source configured to generate a secondary pressure in a secondary pressure range, the secondary pressure less than the primary pressure, the secondary pressure induced by the primary pressure source;
a first valve configured to couple the primary pressure source to the secondary pressure source;
a second valve coupled to the secondary pressure source, the second valve configured to regulate the secondary pressure; and
a control component coupled to, and configured for control of, the reference pressure source, the first valve, and the second valve, the control component further configured to:
run the reference pressure source when pressure in the primary pressure source falls below a lower bound of the primary pressure range;
open the first valve when pressure in the secondary pressure source falls below a lower bound of the secondary pressure range; and
open the second valve when pressure in the secondary pressure source rises above an upper bound of the secondary pressure range.

21. A handheld system, comprising:
a reference pressure source configured to generate a reference pressure;
a primary pressure source coupled to the reference pressure source, the primary pressure source configured to generate a primary pressure in a primary pressure range, the primary pressure less than the reference pressure, the primary pressure induced by the reference pressure source;

a secondary pressure source coupled to the primary pressure source, the secondary pressure source configured to generate a secondary pressure in a secondary pressure range, the secondary pressure less than the primary pressure, the secondary pressure induced by the primary pressure source;

a first valve configured to couple the primary pressure source to the secondary pressure source;

a second valve coupled to the secondary pressure source, the second valve configured to regulate the secondary pressure;

a third valve configured to couple the primary pressure source to a microfluidic component via one or more primary pressure outlets for controlling operation of the microfluidic component; and a fourth valve configured to couple the secondary pressure source to one or more secondary pressure outlets for controlling reagent input to the microfluidic component.

22. A handheld system, comprising:

a reference pressure source configured to generate a reference pressure;

a primary pressure source coupled to the reference pressure source, the primary pressure source configured to generate a primary pressure in a primary pressure range, the primary pressure less than the reference pressure, the primary pressure induced by the reference pressure source;

a secondary pressure source coupled to the primary pressure source, the secondary pressure source configured to generate a secondary pressure in a secondary pressure range, the secondary pressure less than the primary pressure, the secondary pressure induced by the primary pressure source;

a microfluidic component coupled to the primary pressure source and the secondary pressure source; and a control component configured to:
  (i) maintain pressure in the primary pressure source in the primary pressure range for controlling operation of the microfluidic component,
  (ii) maintain the pressure in the secondary pressure source in the second pressure range for controlling reagent input to the microfluidic component, and
  (iii) control reagent input to the microfluidic component by controlling one or more secondary outlets of the secondary pressure source, the one or more secondary outlets configured to be coupled to one or more reagent containers supplying reagents to the microfluidic component.

* * * * *